(12) United States Patent
Bouchard et al.

(10) Patent No.: US 6,384,071 B2
(45) Date of Patent: May 7, 2002

(54) TAXOIDS, THEIR PREPARATION AND PHARMACEUTICAL COMPOSITIONS CONTAINING THEM

(75) Inventors: Hervé Bouchard, Ivry sur Seine; Jean-Dominique Bourzat, Vincennes; Alain Commercon, Vitry-sur-Seine, all of (FR)

(73) Assignee: Aventis Pharma, S.A., Antony (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/759,449

(22) Filed: Jan. 16, 2001

Related U.S. Application Data

(60) Division of application No. 09/126,590, filed on Jul. 31, 1998, now Pat. No. 6,194,582, which is a continuation of application No. 08/477,518, filed on Jun. 7, 1995, now Pat. No. 5,814,658, which is a continuation-in-part of application No. 08/162,984, filed on Dec. 8, 1993.

(30) Foreign Application Priority Data

Dec. 9, 1992 (FR) .............................................. 92 14813

(51) Int. Cl.$^7$ ................... A61K 31/337; C07D 305/14; C07D 407/10; C07D 263/04; C07D 413/10
(52) U.S. Cl. ........................ 514/449; 549/511; 548/215; 548/229
(58) Field of Search ........................... 514/449; 549/511

(56) References Cited

U.S. PATENT DOCUMENTS

| | | |
|---|---|---|
| 5,254,580 A | 10/1993 | Chen et al. |
| 5,294,637 A | 3/1994 | Chen et al. |
| 5,532,388 A | 7/1996 | Bouchard et al. |
| 5,814,658 A | 9/1998 | Bouchard et al. |

FOREIGN PATENT DOCUMENTS

| | | |
|---|---|---|
| WO | WO 94/13654 | 6/1994 |
| WO | WO 94/13655 | 6/1994 |

OTHER PUBLICATIONS

Guéritte–Voegelein et al., "Relationships between the Structure of Taxol Analogues and Their Antimitotic Activity," J. Med. Chem. 1991, 34, 992–998.
Klein et al., "Synthesis of Ring B–Rearranged Taxane Analogs," J. Org. Chem. 1994, 59, 2370–2373.

*Primary Examiner*—T. A. Solola
(74) *Attorney, Agent, or Firm*—Finnegan, Henderson, Farabow, Garrett & Dunner, L.L.P.

(57) ABSTRACT

New taxoids of general formula (I), their preparation, and pharmaceutical compounds containing them.

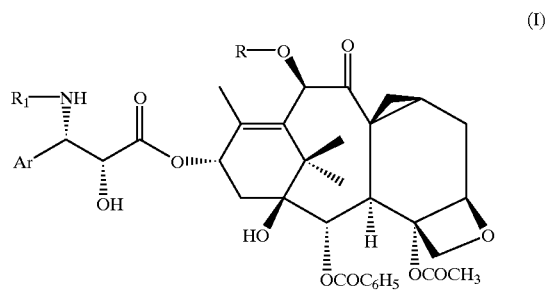

In general formula (I), for example,
Ar represents an aryl radical,
R represents an alkoxyacetyl radical,
$R_1$ represents a benzoyl radical or a radical of formula $R_2$—O—CO— in which $R_2$ represents an optionally substituted alkyl radical, an alkenyl, alkynyl, cycloalkyl, cycloalkenyl, bicycloalkyl, phenyl or heterocyclyl radical.

The new products of general formula (I) have a remarkable antitumor activity.

12 Claims, No Drawings

TAXOIDS, THEIR PREPARATION AND PHARMACEUTICAL COMPOSITIONS CONTAINING THEM

This is a division of application Ser. No. 09/126,590, filed Jul. 31, 1998, now U.S. Pat. No. 6,194,582, which is a continuation of application Ser. No. 08/477,518, filed Jun. 7, 1995, now U.S. Pat. No. 5,814,658 which is a continuation-in-part of application Ser. No. 08/162,984, filed Dec. 8, 1993, all of which are incorporated herein by reference.

The present invention relates to new taxoids of general formula:

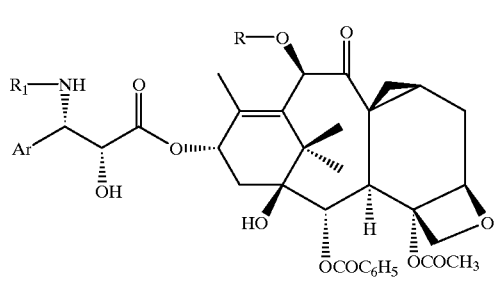

their preparation and pharmaceutical compositions containing them.

In general formula (I),

Ar represents an aryl radical,

R represents a hydrogen atom or an acetyl, alkoxyacetyl or alkyl radical, $R_1$ represents a benzoyl radical or a radical $R_2$—O—CO— in which $R_2$ represents:

a straight or branched alkyl radical containing 1 to 8 carbon atoms; an alkenyl radical containing 2 to 8 carbon atoms; an alkynyl radical containing 3 to 8 carbon atoms; a cycloalkyl radical containing 3 to 6 carbon atoms; a cycloalkenyl radical containing 4 to 6 carbon atoms or a bicycloalkyl radical containing 7 to 11 carbon atoms; these radicals being optionally substituted by one or more substituents chosen from halogen atoms and hydroxy radicals; alkyloxy radicals containing 1 to 4 carbon atoms; dialkylamino radicals in which each alkyl portion contains 1 to 4 carbon atoms; piperidino radicals; morpholino radical; 1-piperazinyl radicals (optionally substituted at position 4 by an alkyl radical containing 1 to 4 carbon atoms or by a phenylalkyl radical whose alkyl portion contains 1 to 4 carbon atoms); cycloalkyl radicals containing 3 to 6 carbon atoms; cycloalkenyl radicals containing 4 to 6 carbon atoms; phenyl radicals; cyano radicals; carboxy radicals or alkyloxycarbonyl radicals whose alkyl portion contains 1 to 4 carbon atoms, or a phenyl radical optionally substituted by one or more atoms or radicals chosen from halogen atoms and alkyl radicals containing 1 to 4 carbon atoms or alkyloxy radicals containing 1 to 4 carbon atoms, or a saturated or unsaturated 4- to 6-membered nitrogen-containing heterocyclyl radical optionally substituted by one or more alkyl radicals containing 1 to 4 carbon atoms, it being understood that the cycloalkyl, cycloalkenyl or bicycloalkyl radicals may be optionally substituted by one or more alkyl radicals containing 1 to 4 carbon atoms.

Preferably, Ar represents a phenyl or α- or β-naphthyl radical optionally substituted by one or more atoms or radicals chosen from halogen atoms (fluorine, chlorine, bromine, or iodine) and alkyl, alkenyl, alkynyl, aryl, arylalkyl, alkoxy, alkylthio, aryloxy, arylthio, hydroxy, hydroxyalkyl, mercapto, formyl, acyl, acylamino, aroylamino, alkoxycarbonylamino, amino, alkylamino, dialkylamino, carboxy, alkoxycarbonyl, carbamoyl, dialkylcarbamoyl, cyano, nitro and trifluoromethyl radicals;

it being understood that the alkyl radicals and the alkyl portions of the other radicals contain 1 to 4 carbon atoms;

that the alkenyl and alkynyl radicals contain 2 to 8 carbon atoms; and that the aryl radicals are phenyl or α- or β-naphthyl radicals or alternatively Ar represents a 5-membered aromatic heterocyclic radical containing one or more hetero atoms, which are identical or different, chosen from nitrogen, oxygen or sulphur atoms;

Ar optionally being substituted by one or more substituents, which are identical or different, chosen from halogen atoms (fluorine, chlorine, bromine or iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl portion contains 1 to 4 carbon atoms, acylamino radicals in which the acyl portion contains 1 to 4 carbon atoms, alkoxycarbonylamino radicals containing 1 to 4 carbon atoms, acyl radicals containing 1 to 4 carbon atoms, arylcarbonyl radicals in which the aryl portion contains 6 to 10 carbon atoms, cyano radicals, carboxy radicals, carbamoyl radicals, alkylcarbamoyl radicals in which the alkyl portion contains 1 to 4 carbon atoms, dialkylcarbamoyl radicals in which each alkyl portion contains 1 to 4 carbon atoms or alkoxycarbonyl radicals in which the alkoxy portion contains 1 to 4 carbon atoms.

More particularly, Ar represents a phenyl, 2- or 3-thienyl or 2- or 3-furyl radical optionally substituted by one or more atoms or radicals, which are identical or different, chosen from halogen atoms, and alkyl, alkoxy, amino, alkylamino, dialkylamino, acylamino, alkoxycarbonylamino and trifluoromethyl radicals.

Still more particularly, Ar represents a phenyl radical optionally substituted by a chlorine or fluorine atom or by an alkyl (methyl), alkoxy (methoxy), dialkylamino (diethylamino), acylamino (acetylamino) or alkoxycarbonylamino (tert-butoxycarbonylamino) or 2- or 3-thienyl or 2- or 3-furyl radical.

Regarding the alkoxyacetyl radical for R, the alkoxy portion thereof preferably contains 1 to 8 carbon atoms and, more preferably, 1 to 4 carbon atoms. The alkoxy portion may be linear or branched. Preferred alkoxyacetyl groups include saturated groups such as methoxyacetyl ($CH_3OCH_2C(O)$—), ethoxyacetyl ($CH_3CH_2OCH_2C(O)$—), isopropoxyacetyl (($CH_3)_2CHOCH_2C(O)$—), and butoxyacetyl ($CH_3CH_2CH_2CH_2OCH_2C(O)$—).

Of even more special interest are the products of general formula (I) in which Ar represents a phenyl or 3-thienyl radical and $R_1$ represents a benzoyl or tert-butoxycarbonyl radical.

According to the present invention, the new taxoids of general formula (I) can be obtained from a product of general formula:

(II)

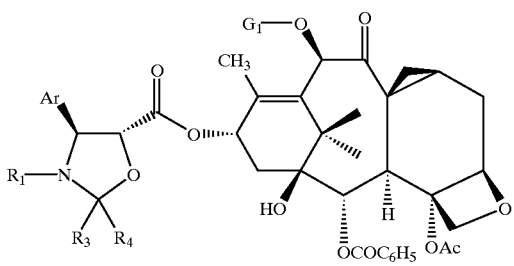

in which Ar and $R_1$ are defined as above, and $R_3$ and $R_4$, which are identical or different represent a hydrogen atom or an alkyl radical containing 1 to 4 carbon atoms, or an aralkyl radical whose alkyl portion contains 1 to 4 carbon atoms and the aryl portion preferably represents a phenyl radical optionally substituted by one or more alkoxy radicals containing 1 to 4 carbon atoms, or an aryl radical preferably representing a phenyl radical optionally substituted by one or more alkoxy radicals containing 1 to 4 carbon atoms, or alternatively $R_3$ represents an alkoxy radical containing 1 to 4 carbon atoms or a trihalomethyl radical such as trichloromethyl or a phenyl radical substituted by a trihalomethyl radical such as trichloromethyl and $R_4$ represents a hydrogen atom, or alternatively $R_3$ and $R_4$ form, together with the carbon atom to which they are attached, a 4- to 7-membered ring, and $G_1$ represents a hydrogen atom or an acetyl, alkoxyacetyl or alkyl radical or a hydroxy-protecting group, the procedure being carried out, according to the meanings of $R_3$ and $R_4$, in the following manner:

1) when $R_3$ represents a hydrogen atom or an alkoxy radical containing 1 to 4 carbon atoms or an optionally substituted aryl radical and $R_4$ represents a hydrogen atom, the product of general formula (II) is treated in acidic medium in order to obtain a product of general formula:

(III)

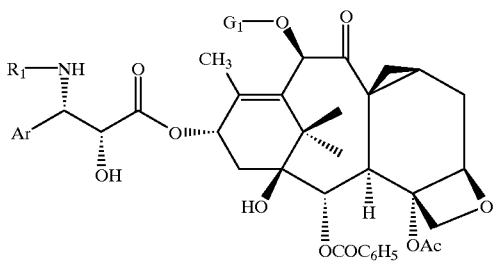

in which Ar, $R_1$ and $G_1$ are defined as above, whose $G_1$ radical is, if necessary, replaced by a hydrogen atom or an alkoxyacetyl radical, said alkoxyacetyl radical being obtained by action of an alkoxyacetic acid or derivative thereof on a compound of formula (III) wherein $G_1$ represents a hydrogen atom.

Regarding the alkoxyacetyl radical for $G_1$, the alkoxy portion thereof preferably contains 1 to 8 carbon atoms and, more preferably, 1 to 4 carbon atoms. The alkoxy portion may be linear or branched. Preferred alkoxyacetyl groups include saturated groups such as methoxyacetyl ($CH_3OCH_2C(O)$—), ethoxyacetyl ($CH_3CH_2OCH_2C(O)$—), isopropoxyacetyl (($CH_3)_2CHOCH_2C(O)$—), and butoxyacetyl ($CH_3CH_2CH_2CH_2OCH_2C(O)$—).

The deprotection of the side chain of the product of general formula (II) can also be carried out in the presence of an inorganic acid (hydrochloric acid or sulphuric acid) or an organic acid (acetic acid, methanesulphonic acid, trifluoromethanesulphonic acid or p-toluenesulphonic acid), used alone or in the form of a mixture, the procedure being carried out in an organic solvent chosen from alcohols (methanol, ethanol or isopropanol), ethers (tetrahydrofuran, diisopropyl ether or methyl t-butyl ether), esters (ethyl acetate, isopropyl acetate or n-butyl acetate), aliphatic hydrocarbons (pentane, hexane or heptane), halogenated aliphatic hydrocarbons (dichloromethane or 1,2-dichloroethane), aromatic hydrocarbons (benzene, toluene or xylenes) and nitriles (acetonitrile) at a temperature ranging from −10 to 60° C., preferably from 15 to 30° C. The acid may be used in a catalytic or stoichiometric quantity or in excess.

The deprotection can also be carried out under oxidizing conditions, using for example ammonium cerium(IV) nitrate in an acetonitrile-water mixture or 2,3-dichloro-5,6-dicyano-1,4-benzoquinone in water.

The deprotection can also be carried out under reducing conditions, for example by hydrogenolysis in the presence of a catalyst.

When $G_1$ represents a protecting group, it is preferably a 2,2,2-trichloroethoxycarbonyl or 2-(2-trichloromethylpropoxy) carbonyl radical whose replacement by a hydrogen atom is carried out using zinc, optionally combined with copper, in the presence of acetic acid, at a temperature ranging from 20 to 60° C. or by means of an inorganic or organic acid such as hydrochloric acid or acetic acid in a solution in an aliphatic alcohol containing 1 to 3 carbon atoms or in an aliphatic ester such as ethyl acetate, isopropyl acetate or n-butyl acetate in the presence of zinc optionally combined with copper, or alternatively, when $G_1$ represents an alkoxyacetyl radical, its optional replacement by a hydrogen atom is carried out by treatment in alkaline medium or by the action of a zinc halide under conditions which do not affect the rest of the molecule. Generally, the alkaline treatment is carried out by the action of ammonia in aqueous-alcoholic medium, at a temperature close to 20° C. Generally, the treatment with a zinc halide, preferably zinc iodide, is carried out in methanol at a temperature close to 20° C.

2) when $R_3$ and $R_4$, which are identical or different, represent an alkyl radical containing 1 to 4 carbon atoms, or an aralkyl radical whose alkyl portion contains 1 to 4 carbon atoms and the aryl portion is preferably an optionally substituted phenyl radical, or alternatively $R_3$ represents a trihalomethyl radical or a phenyl radical substituted by a trihalomethyl radical and $R_4$ represents a hydrogen atom, or alternatively $R_3$ and $R_4$ form, together with the carbon atom to which they are attached, a 4- to 7-membered ring, the product of general formula (II) is converted to the product of general formula:

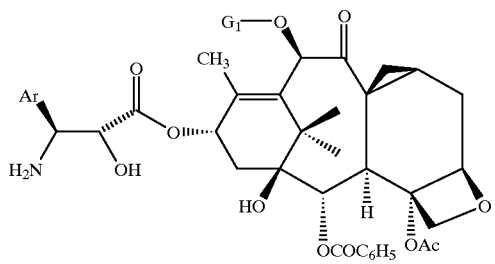

(IV)

in which Ar and $G_1$ are defined as above, which is acylated by means of benzoyl chloride or a reactive derivative of general formula:

$$R_2—O—CO—X \quad (V)$$

in which $R_2$ is defined as above and X represents a halogen atom (fluorine or chlorine) or a residue $—O—R_2$ or $—O—CO—O—R_2$, to give a product of general formula (III) in which Ar, $R_1$ and $G_1$ are defined as above, whose $G_1$ radical is, if necessary, replaced by a hydrogen atom and then by an alkoxyacetyl radical, said alkoxyacetyl radical being obtained by action of an alkoxyacetic acid or a derivative therof on a compound represented by the formula (I) wherein R represents a hydrogen atom.

The products of general formula (IV) can be obtained by treating a product of general formula (II), in which Ar, $R_1$ and $G_1$ are defined as above, $R_3$ and $R_4$, which are identical or different, represent an alkyl, aralkyl or aryl radical, or alternatively $R_3$ and $R_4$ form together with the carbon atom to which they are attached a 4- to 7-membered ring, with an inorganic acid (preferably hydrochloric acid or sulphuric acid) or an organic acid (preferably formic acid) optionally in an alcohol containing 1 to 3 carbon atoms (preferably methanol, ethanol or isopropanol) at a temperature ranging from 0 to 50° C. Preferably, formic acid is used at a temperature close to 20° C.

The acylation of the product of general formula (IV) by means of benzoyl chloride or a reactive derivative of general formula (V) is carried out in an inert organic solvent chosen from esters such as ethyl acetate, isopropyl acetate or n-butyl acetate and halogenated aliphatic hydrocarbons such as dichloromethane or 1,2-dichloroethane in the presence of an inorganic base such as sodium bicarbonate or an organic base such as triethylamine. The reaction is carried out at a temperature ranging from 0 to 50° C., preferably close to 20° C.

When the radical $G_1$ represents a protecting group, its replacement by a hydrogen atom is carried out under the conditions described above.

The products of general formula (II) can be obtained according to one of the following methods:

1) by esterification of the product of general formula:

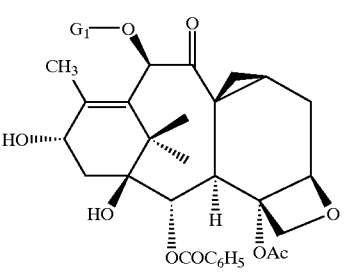

(VI)

in which $G_1$ is defined as above, by means of an acid of general formula:

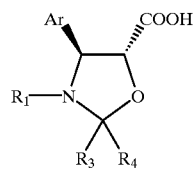

(VII)

in which Ar, $R_1$, $R_3$ and $R_4$ are defined as above, or of a derivative of this acid.

The esterification by means of an acid of general formula (VII) can be carried out in the presence of a condensing agent (carbodiimide, reactive carbonate) and an activating agent (aminopyridine) in an organic solvent (ether, ester, ketones, nitriles, aliphatic hydrocarbons, halogenated aliphatic hydrocarbons or aromatic hydrocarbons) at a temperature ranging from −10 to 90° C.

The esterification may also be performed using the acid of general formula (VII) in anhydride form, the procedure being carried out in the presence of an activating agent (aminopyridine) in an organic solvent (ethers, esters, ketones, nitriles, aliphatic hydrocarbons, halogenated aliphatic hydrocarbons or aromatic hydrocarbons) at a temperature ranging from 0 to 90° C.

The esterification can also be performed using the acid of general formula (VII) in halide form or in anhydride form with an aliphatic or aromatic acid, optionally prepared in situ, in the presence of a base (tertiary aliphatic amine), the procedure being carried out in an organic solvent (ethers, esters, ketones, nitriles, aliphatic hydrocarbons, halogenated aliphatic hydrocarbons or aromatic hydrocarbons) at a temperature ranging from 0 to 80° C.

The acid of general formula (VII) can be obtained by saponification of an ester of general formula:

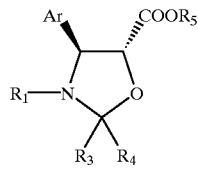

(VIII)

in which Ar, $R_1$, $R_3$ and $R_4$ are defined as above and $R_5$ represents an alkyl radical containing 1 to 4 carbon atoms optionally substituted by a phenyl radical.

Generally, the saponification is carried out by means of an inorganic base (alkali metal hydroxide, carbonate or bicarbonate) in aqueous-alcoholic medium (methanol-water) at a temperature ranging from 10 to 40° C.

The ester of general formula (VIII) can be obtained by the action of a product of general formula:

(IX)

in which $R_3$ and $R_4$ are defined as above in the form of a dialkylacetal or an enol alkyl ether, on an ester of general formula:

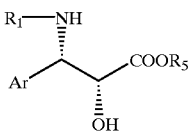

(X)

in which Ar, $R_1$ and $R_5$ are defined as above, the procedure being carried out in an inert organic solvent (aromatic hydrocarbon) in the presence of a strong inorganic acid (sulphuric acid) or organic acid (p-toluenesulphonic acid optionally in the form of a pyridinium salt) at a temperature ranging from 0° C. to the boiling temperature of the reaction mixture.

The ester of general formula (X) can be obtained by the action of a product of general formula (V) on an ester of general formula:

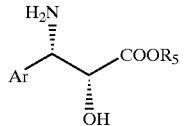

(XI)

in which Ar and $R_5$ are defined as above, the procedure being carried out in an organic solvent (ester, halogenated aliphatic hydrocarbon) in the presence of an inorganic or organic base at a temperature ranging from 0 to 50° C.

The product of general formula (XI) can be obtained by reduction of an azide of general formula:

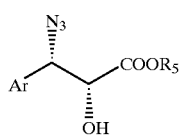

(XII)

in which Ar and $R_5$ are defined above, by means of hydrogen in the presence of a catalyst such as palladium on carbon, the procedure being carried out in an organic solvent (ester).

The product of general formula (XII) can be obtained by the action of an azide such as trimethylsilyl azide in the presence of zinc chloride or alkali metal (sodium, potassium or lithium) azide in aqueous-organic medium (water-tetrahydrofuran) at a temperature ranging from 20° C. to the boiling temperature of the reaction mixture, on an epoxide of general formula:

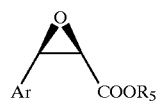

(XIII)

in which Ar and $R_5$ are defined as above, optionally prepared in situ.

The epoxide of general formula (XIII) can be obtained, optionally in situ, by dehydrohalogenation of a product of general formula:

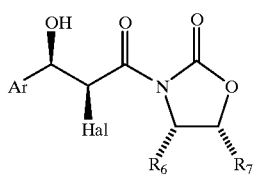

(XIV)

in which Ar is defined as above, Hal represents a halogen atom, preferably a bromine atom, and $R_6$ and $R_7$, which are identical or different, represent a hydrogen atom or an alkyl radical containing 1 to 4 carbon atoms or a phenyl radical, at least one being an alkyl radical or a phenyl radical, by means of a alkali-metal alcoholate, optionally prepared in situ, in an inert organic solvent such as tetrahydrofuran at a temperature ranging from −80° C. to 25° C.

The product of general formula (XIV) can be obtained by the action of an aldehyde of general formula:

Ar—CHO (XV)

in which Ar is defined as above, on a halide of general formula:

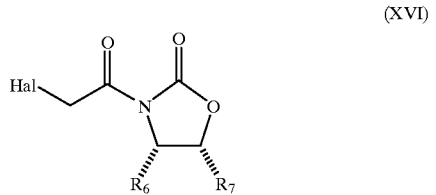

(XVI)

in which Hal, $R_6$ and $R_7$ are defined as above, anionized beforehand.

Generally, the procedure is carried out in an inert organic solvent chosen from ethers (ethyl ether) and halogenated aliphatic hydrocarbons (methylene chloride) at a temperature ranging from −80 to 25° C., in the presence of a tertiary amine (triethylamine) and an enolysing agent (di-n-butylboron triflate).

The product of general formula (XVI) can be obtained by the action of a halide of a haloacetic acid, preferably bromoacetic acid bromide, on the corresponding oxazolidi-none.

The product of general formula (XI) can be obtained by hydrogenolysis of a product of general formula:

(XVII)

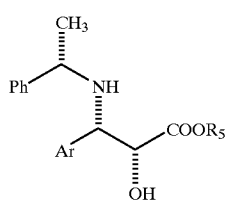

in which Ar and $R_5$ are defined as above and Ph represents an optionally substituted phenyl radical.

Generally, the hydrogenolysis is carried out by means of hydrogen in the presence of a catalyst. More particularly, palladium on carbon containing 1 to 10% by weight of palladium or palladium dihydroxide containing 20% by weight of palladium is used as catalyst.

The hydrogenolysis is carried out in an organic solvent or in a mixture of organic solvents. It is advantageous to carry out the procedure in acetic acid optionally combined with an aliphatic alcohol containing 1 to 4 carbon atoms such as a mixture of acetic acid-methanol at a temperature ranging from 20 to 80° C.

The hydrogen necessary for the hydrogenolysis can also be provided by a compound which liberates hydrogen by chemical reaction or by thermal decomposition (ammonium formate). It is advantageous to carry out the procedure at a hydrogen pressure ranging from 1 to 50 bar.

The product of general formula (XVII) can be obtained by hydrolysis or alcoholysis of a product of general formula:

(XVIII)

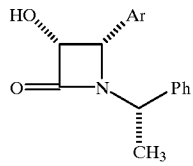

in which Ar and Ph are defined as above.

It is particularly advantageous to carry out an alcoholysis by means of an alcohol of formula $R_5$—OH in which $R_5$ is defined as above, the procedure being carried out in acidic medium.

Preferably, the alcoholysis is carried out by means of methanol in the presence of a strong inorganic acid such as hydrochloric acid at a temperature close to the reflux temperature of the reaction mixture.

The product of general formula (XVIII) can be obtained by saponification of an ester of general formula:

(XIX)

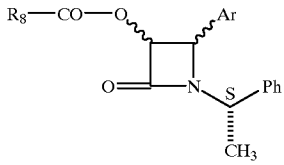

in which Ar and Ph are defined as above and $R_8$ represents an alkyl, phenylalkyl or phenyl radical, followed by separation of the 3R, 4S diastereoisomer of general formula (XVII) from the other diastereoisomers.

Generally, the saponification is carried out by means of an inorganic or organic base such as ammonium hydroxide, lithium hydroxide, sodium hydroxide or potassium hydroxide in a suitable solvent such as a methanol-water or tetrahydrofuran-water mixture at a temperature ranging from −10° C. to 20° C.

The separation of the 3R, 4S diastereoisomer can be carried out by selective crystallization from a suitable organic solvent such as ethyl acetate.

The product of general formula (XIX) can be obtained by cycloaddition of an imine of general formula:

(XX)

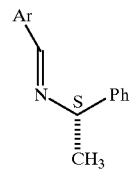

in which Ar and Ph are defined as above, onto an acid halide of general formula:

(XXI)

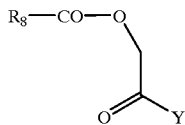

in which $R_8$ is defined as above and Y represents a halogen atom such as a bromine or chlorine atom.

Generally, the reaction is carried out at a temperature ranging from 0 to 50° C. in the presence of a base chosen from aliphatic tertiary amines (triethylamine) or pyridine in an organic solvent chosen from optionally halogenated aliphatic hydrocarbons (methylene chloride or chloroform) and aromatic hydrocarbons (benzene, toluene or xylenes).

The product of general formula (XX) can be obtained under conditions analogous to those described by M. Furukawa et al., Chem. Phar. Bull., 25 (1), 181–184 (1977).

The product of general formula (VI) can be obtained by the action of an alkali metal halide (sodium iodide or potassium fluoride) or an alkali metal azide (sodium azide) or a quaternary ammonium salt or an alkali metal phosphate, on a baccatin III or 10-deacetylbaccatin III derivative of general formula:

(XXII)

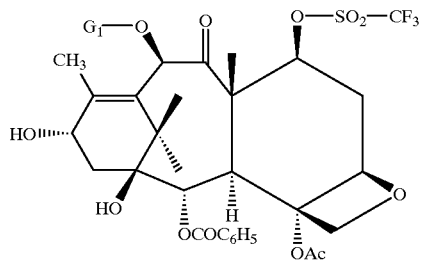

in which $G_1$ is defined as above.

Generally, the reaction is carried out in an organic solvent chosen from ethers (tetrahydrofuran, diisopropyl ether, methyl t-butyl ether) and nitriles (acetonitrile), alone or in the form of a mixture, at a temperature ranging from 20° C. to the boiling temperature of the reaction mixture.

The product of formula (XXII) in which $G_1$ represents a hydrogen atom or an acetyl, alkoxyacetyl or alkyl radical can be obtained by the action of a trifluoromethanesulphonic acid derivative such as the anhydride or N-phenyltrifluoromethanesulphonimide, on baccatin III or 10-deacetylbaccatin III, which can be extracted according to known methods from yew leaves (Taxus baccata), optionally followed by protection in position 10, it being understood that in order to obtain a product of general formula (XXII) in which $G_1$ represents an alkoxyacetyl or alkyl radical, it is necessary to treat beforehand the 10-deacetylbaccatin III protected in position 7, preferably with a silylated radical, with an alkoxy acetic acid halide or with an alkyl halide.

Generally, the reaction of a trifluoromethanesulphonic acid derivative is carried out in an inert organic solvent (optionally halogenated aliphatic hydrocarbons, or aromatic hydrocarbons) in the presence of an organic base such as an aliphatic tertiary amine (triethylamine) or pyridine, at a temperature ranging from –50 to +20° C.

Generally, the introduction of an alkoxyacetyl group is carried out by treating the protected 10-deacetylbaccatin III with an alkoxyacetic acid halide, the procedure being carried out in a basic organic solvent such as pyridine at a temperature close to 20° C.

Generally, the introduction of an alkyl radical is carried out by treating the 10-deacetylbaccatin III, protected and metallized in position 10, by means, for example, of a alkali metal hydride (sodium hydride) or a metallic alkylide (butyllithium), with an alkyl halide.

2) by the action of an alkali metal halide (sodium iodide or potassium fluoride) or an alkali metal azide (sodium azide) or a quaternary ammonium salt or an alkali metal phosphate on a product of general formula:

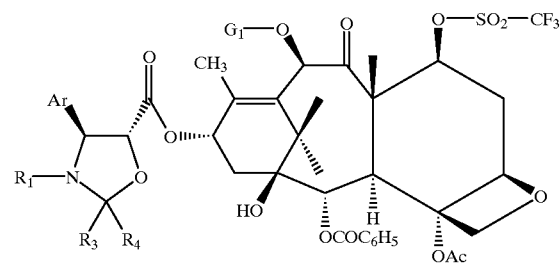

(XXIII)

in which Ar, $R_1$, $R_3$, $R_4$ and $G_1$ are defined as above.

Generally, the reaction is carried out in an organic solvent chosen from ethers (tetrahydrofuran, diisopropyl ether or methyl t-butyl ether) and nitriles (acetonitrile), alone or in the form of a mixture, at a temperature ranging from 20° C. to the boiling temperature of the reaction mixture.

The product of general formula (XXIII) can be obtained by the action of a trifluoromethanesulphonic acid derivative such as the anhydride or N-phenyltrifluoromethanesulphonimide on a taxoid of general formula:

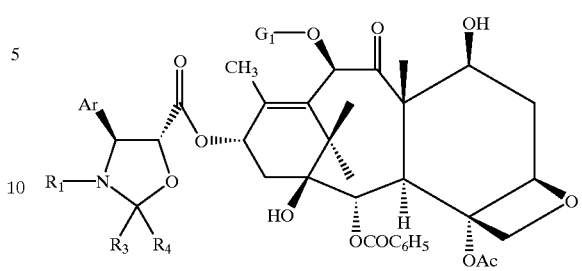

(XXIV)

in which Ar, $R_1$, $R_3$, $R_4$ and $G_1$ are defined as above.

Generally, the reaction is carried out in an inert organic solvent (optionally halogenated aliphatic hydrocarbons, or aromatic hydrocarbons) in the presence of an organic base such as an aliphatic tertiary amine (triethylamine) or pyridine, at a temperature ranging from –50 to +20° C.

The taxoid of general formula (XXIV), in which $G_1$ represents a hydrogen atom or an alkoxyacetyl radical, can be obtained from a product of general formula:

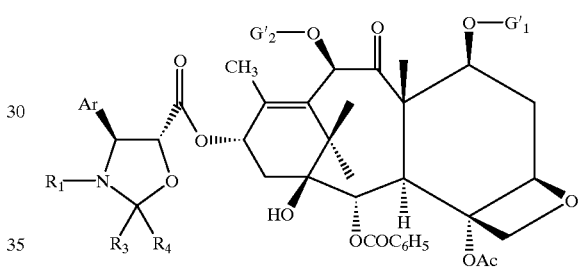

(XXV)

in which Ar, $R_1$, $R_3$, $R_4$ are defined as above, $G'_1$ represents a hydroxy-protecting group and $G'_2$ represents an alkoxyacetyl radical or a hydroxy-protecting group, by replacement of the protecting group $G'_1$ by a hydrogen atom and optionally $G'_2$ by a hydrogen atom and then by an alkoxyacetyl radical, said alkoxyacetyl radical being obtained by action of an alkoxyacetic acid or a derivative thereof on a compound represented by the formula (I) wherein R represents a hydrogen atom.

The radicals $G'_1$ and G'2 when they represent a hydroxy-protecting group are preferably 2,2,2-trichloroethoxycarbonyl or 2-(trichloromethyl-propoxy) carbonyl radicals or trialkylsilyl, dialkylarylsilyl, alkyldiarylsilyl or triarylsilyl radicals in which the alkyl portions contain 1 to 4 carbon atoms and the aryl portions are preferably phenyl radicals, it being possible, in addition, for $G'_2$ to represent an alkoxyacetyl radical.

When $G'_1$ and $G'_2$ represent a 2,2,2-trichloroethoxycarbonyl or 2-(2-trichloromethylpropoxy) carbonyl radical, the replacement of the protecting groups by hydrogen atoms is carried out using zinc, optionally combined with copper, in the presence of acetic acid at a temperature ranging from 20 to 60° C. or by means of an inorganic or organic acid such as hydrochloric acid or acetic acid in solution in an aliphatic alcohol containing 1 to 3 carbon atoms or an aliphatic ester such as ethyl acetate, isopropyl acetate or n-butyl acetate in the presence of zinc optionally combined with copper.

When $G'_1$ represents a silylated radical and $G'_2$ represents an alkoxyacetyl radical, the replacement of the protecting group $G'_1$ by a hydrogen atom can be carried out by means of, for example, gaseous hydrochloric acid in ethanolic solution at a temperature close to 0° C., under conditions which are without effect on the rest of the molecule.

When $G'_2$ represents an alkoxyacetyl radical, its optional replacement by a hydrogen atom is carried out by treatment in alkaline medium or by the action of a zinc halide under conditions which do not affect the rest of the molecule. Generally, the alkaline treatment is carried out by the action of ammonia in aqueous-alcoholic medium, at a temperature close to 20° C. Generally, the treatment with a zinc halide, preferably zinc iodide, is carried out in methanol at a temperature close to 20° C., The product of general formula (XXV) can be obtained under the conditions described in international application PCT/WO 9209589, the disclosure of which is incorporated by reference herein.

The new derivatives of general formula (I) can also be obtained by esterification of a product of general formula (VI) by means of an acid of general formula:

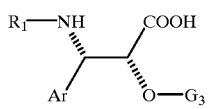

(XXVI)

in which Ar and $R_1$ are defined as above and $G_3$ represents a hydroxy-protecting group chosen from methoxymethyl, 1-ethoxyethyl, benzyloxymethyl, (β-trimethylsilyloxy) methyl, tetrahydropyranyl, 2,2,2-trichloroethoxymethyl, 2,2,2-trichloroethoxycarbonyl or 2-(2-trichloromethylpropoxy)carbonyl radicals or $CH_2$—Ph radicals in which Ph represents a phenyl radical optionally substituted by one or more atoms or radicals, which are identical or different, chosen from halogen atoms and alkyl radicals containing 1 to 4 carbon atoms or alkoxy radicals containing 1 to 4 carbon atoms, or an activated derivative of this acid, to give a product of general formula:

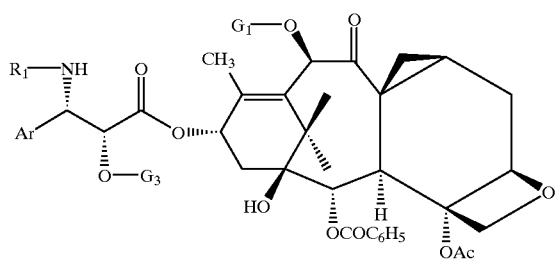

(XXVII)

in which Ar, $R_1$, $G_1$, and $G_3$ are defined as above, followed by the replacement of the protecting group $G_3$ by hydrogen atom and optionally $G_1$ by a hydrogen atom and then by an alkoxyacetyl radical, said alkoxyacetyl radical being obtained by action of an alkoxyacetic acid or a derivative thereof on a compound represented by the formula (I) wherein R represents a hydrogen atom.

The esterification can be performed under the conditions described above for the esterification of the product of general formula (VI) by means of an acid of general formula (VII).

The replacement of the protecting groups $G_1$ and $G_3$ of the product of general formula (XXVII) by a hydrogen atom is carried out by treatment with zinc, optionally combined with copper, in the presence of acetic acid at a temperature ranging from 30 to 60° C. or by means of an inorganic or organic acid such as hydrochloric acid or acetic acid in solution in an aliphatic alcohol containing 1 to 3 carbon atoms or an aliphatic ester such as ethyl acetate, isopropyl acetate or n-butyl acetate in the presence of zinc optionally combined with copper, when $G_1$ and $G_3$ represent a 2,2,2-trichloroethoxycarbonyl or 2-(2-trichloromethylpropoxy) carbonyl radical. The replacement of the protecting group $G_3$, when it represents a silylated radical or an acetal residue, can be carried out by treatment in acidic medium such as for example hydrochloric acid in solution in an aliphatic alcohol containing 1 to 3 carbon atoms (methanol, ethanol, propanol or isopropanol) or aqueous hydrofluoric acid at a temperature ranging from 0 to 40° C., when it represents an acetal residue, the replacement of the Protecting group $G_1$ then being carried out under the conditions described above. When $G_3$ represents a group —$CH_2$—Ph, the replacement of this protecting group with a hydrogen atom can be carried out by hydrogenolysis in the presence of a catalyst.

The acid of general formula (XXVI) can be obtained by saponification of an ester of general formula:

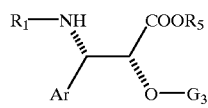

(XXVIII)

in which Ar, $R_1$, $R_5$ and $G_3$ are defined as above.

Generally, the saponification is carried out by means of an inorganic base (alkali metal hydroxide, carbonate or bicarbonate) in aqueous-alcoholic medium (methanol-water) at a temperature ranging from 10 to 40° C.

The ester of general formula (XXVIII) can be obtained according to the usual methods for the preparation of ethers, and more particularly according to the procedures described by J.-N. DENIS et al., J. Org. Chem., 51 46–50 (1986), from a product of general formula (XI).

Compounds of the formula (I)

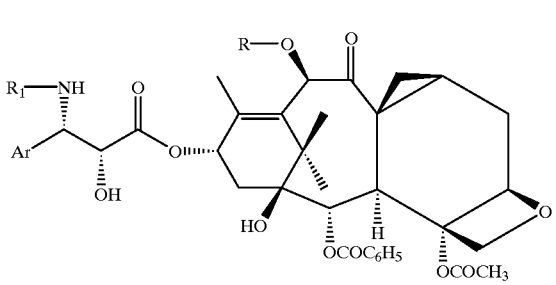

(I)

in which R represents an alkoxyacetyl radical, $R_1$ represents a benzoyl radical or a radical $R_2$—O—CO in which $R_2$ represents an alkyl, alkenyl, alkynyl, cycloalkyl, cycloalkenyl, bicycloalkyl, phenyl or heterocyclyl radical, and Ar represents an aryl radical, may be made by a process comprising esterifying a compound of the formula (XXIX):

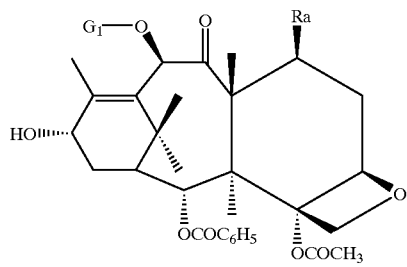

(XXIX)

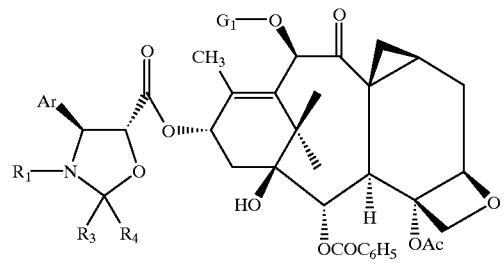

(II)

in which $G_1$ represents an alkoxyacetyl radical or other hydroxy-protecting group and Ra represents a radical $O—SO_2—CF_3$ or forms, together with the carbon atom of the α methyl group, a cyclopropyl ring, with a lactam of the formula (XXX):

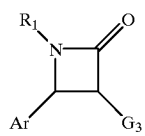

(XXX)

wherein $G_3$ is a hydroxy-protecting group chosen from methoxymethyl, 1-ethoxyethyl, benzyloxymethyl, (β-trimethylsilyloxy)methyl, tetrahydropyranyl, 2,2,2-trichloroethoxymethyl, 2,2,2-trichloroethoxycarbonyl or 2-(2-trichloromethylpropoxy)carbonyl radicals, or $CH_2—$Ph radicals in which Ph represents a phenyl radical optionally substituted by one or more atoms or radicals, which are identical or different, chosen from halogen atoms and alkyl radicals containing 1 to 4 carbon atoms or alkoxy radicals containing 1 to 4 carbon atoms, and Ar and $R_1$ are defined as above, optionally transforming the $O—SO_2—CF_3$ radical into a cyclopropyl ring; and replacing $G_3$ by a hydrogen atom and optionally $G_1$ by a hydrogen atom, said method comprising the further step, if $G_1$ is replaced by a hydrogen atom, of converting said $G_1$ hydrogen atom to an alkoxyacetyl radical by action of an alkoxyacetic acid or derivative thereof on a compound obtained after replacement of $G_1$ by said hydrogen atom.

Compounds of the formula (I):

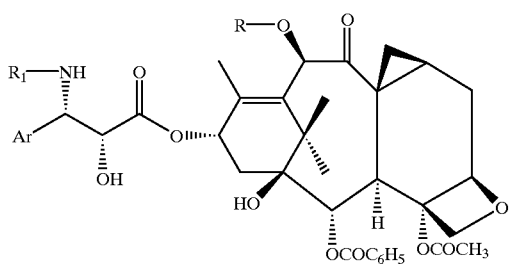

(I)

wherein R represents butoxyacetyl, ethoxyacetyl, and isopropoxyacetyl, $R_1$ represents a t-butoxycarbonyl radical, and Ar represents phenyl, may be made by the process comprising esterifying with an alkoxyacetic acid or derivative thereof, a compound of the formula (II):

wherein $G_1$ represents a hydrogen atom, and $R_3$ and $R_4$, which are identical or different, represent a hydrogen atom or an alkyl radical containing 1 to 4 carbon atoms, or an aralkyl radical whose alkyl portion contains 1 to 4 carbon atoms and the aryl portion preferably represents a phenyl radical optionally substituted by one or more alkoxy radicals containing 1 to 4 carbon atoms, or an aryl radical preferably representing a phenyl radical optionally substituted by one or more alkoxy radicals containing 1 to 4 carbon atoms, or alternatively $R_3$ represents an alkoxy radical containing 1 to 4 carbon atoms or a trihalomethyl radical such as trichloromethyl or a phenyl radical substituted by a trihalomethyl radical such as trichloromethyl and $R_4$ represents a hydrogen atom, or alternatively $R_3$ and $R_4$ form, together with the carbon atom to which they are attached, a 4- to 7-membered ring, and opening the oxazaldine ring portoin of the compound of formula (II) to obtain the compound of formula (I).

Compounds of the formula (I):

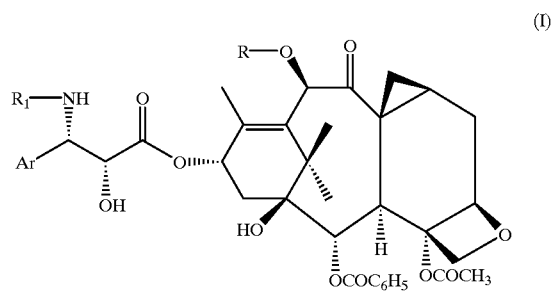

(I)

in which R represents an alkoxyacetyl radical, $R_1$ represents a benzoyl radical or a radical $R_2—O—CO$ in which $R_2$ represents an alkyl, alkenyl, alkynyl, cycloalkyl, cycloalkenyl, bicycloalkyl, phenyl or heterocyclyl radical, and Ar represents an aryl radical, may be made by a process comprising esterifying a compound of the formula (XXIX):

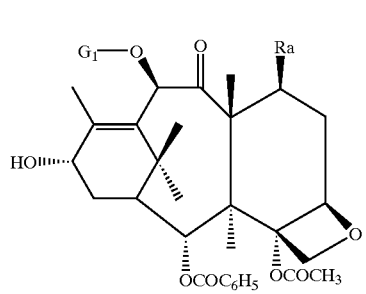

(XXIX)

in which $G_1$ represents an alkoxyacetyl radical or other hydroxy-protecting group and Ra represents a radical $O—SO_2—CF_3$ or forms, together with the carbon atom of the α methyl group, a cyclopropyl ring, with a free acid of the formula (VII):

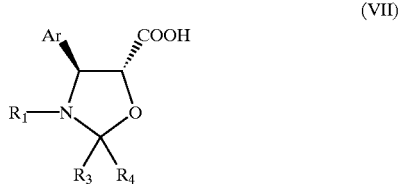

(VII)

in which $R_3$ and $R_4$, which are identical or different represent a hydrogen atom or an alkyl radical containing 1 to 4 carbon atoms, or an aralkyl radical whose alkyl portion contains 1 to 4 carbon atoms and the aryl portion preferably represents a phenyl radical optionally substituted by one or more alkoxy radicals containing 1 to 4 carbon atoms, or an aryl radical preferably representing a phenyl radical optionally substituted by one or more alkoxy radicals containing 1 to 4 carbon atoms, or alternatively $R_3$ represents an alkoxy radical containing 1 to 4 carbon atoms or a trihalomethyl radical such as trichloromethyl or a phenyl radical substituted by a trihalomethyl radical such as trichloromethyl and $R_4$ represents a hydrogen atom, or alternatively $R_3$ and $R_4$ form, together with the carbon atom to which they are attached, a 4- to 7-membered ring; and Ar and $R_1$ are defined as above, optionally transforming the O—$SO_2$—$CF_3$ radical into a cyclopropyl ring, and removing, if $G_1$ is said other hydroxy-protecting group, said hydroxy-protecting group to obtain a hydrogen atom and converting said hydrogen atom to an alkoxyacetyl radical by action of an alkoxyacetic acid or derivative thereof on said compound obtained after replacement of said $G_1$ hydroxy-protecting group by a hydrogen atom.

The new products of general formula (I) obtained using the procedures according to the invention can be purified according to known methods such as crystallization or chromatography.

The products of general formula (I) have remarkable biological properties.

In vitro, measurement of the biological activity is carried out on tubulin extracted from pig brain by the method of M. L. Shelanski et al., Proc. Natl. Acad. Sci. USA, 70, 765–768 (1973). The study of the depolymerization of the microtubules into tubulin is carried out according to the method of G. Chauviére et al., C. R. Acad. Sci., 293, série II, 501–503 (1981). In this study, the products of general formula (I) proved at least as active as taxol and Taxotere.

In vivo, the products of general formula (I) proved active in mice grafted with the B16 melanoma at doses ranging from 1 to 10 mg/kg intraperitoneally, as well as on other liquid or solid tumours.

The new compounds have anti-tumor properties, more particularly, activity against tumors which are resistant to Taxol® and Taxotere®. Such tumors include, for example, colon tumors which have an elevated expression of mdr 1 gene (multi-drug resistant gene). Multi-drug resistance is the usual term relating to the resistance by a tumor against various compounds having differing structures and mechanisms of action. Taxoids are generally known to be highly recognized by experimental tumors such as P388/DOX, a P388 murine leukemia cell line selected for doxorubicin (DOC) resistance, which express mdr 1. The new compounds according to the present invention are less recognized by P388/DOX. More particularly, the new compounds are less recognized than Taxotere® by mdr 1.

In particular, it has been found that the new compounds of the present invention including the compounds of example 1, example 2 and example 3 have better multi-drug resistance properties than Taxol® and Taxotere®. Additionally, it has surprisingly been found that the compound of example 3 has substantially better multi-drug resistance properties than the compounds of example 1 and example 2.

The following Examples 1–5 provide general illustration and Examples 6–10 illustrate the present invention:

Example 1

A solution of 2.01 g of 4-acetoxy-2α-benzoyloxy-5β,20-epoxy-1β,10β-dihydroxy-7β,8β-methylene-9-oxo-19-nor-11-taxen-13α-yl (4S,5R)-3-tert-butoxycarbonyl-2,2-dimethyl-4-phenyl-5-oxazolidinecarboxylate in 20 cm³ of formic acid is stirred for 4 hours at a temperature close to 20° C. and then concentrated to dryness under reduced pressure (0.27 kPa) at 40° C. The foam obtained is dissolved in 100 cm³ of dichloromethane and the solution obtained is supplemented with 20 cm³ of a saturated aqueous sodium hydrogen carbonate solution. The aqueous phase is separated after settling has taken place and extracted with 20 cm³ of dichloromethane. The organic phases are pooled, dried over magnesium sulphate, filtered and then concentrated to dryness under reduced pressure (2.7 kPa) at 40° C. 1.95 g of a white foam are obtained which are purified by chromatography on 200 g of silica (0.063–0.2 mm) contained in a column 7 cm in diameter, eluting with a dichloromethane-methanol mixture (98-2 by volume) and collecting 30 cm³ fractions. The fractions containing only the desired product are pooled and concentrated to dryness under reduced pressure (0.27 kPa) at 40° C. for 2 hours. 1.57 g of 4-acetoxy-2α-benzoyloxy-5β,20-epoxy-1β,10β-dihydroxy-7β,8β-methylene-9-oxo-19-nor-11-taxen-13α-yl (2R,3S)-3-amino-2-hydroxy-3-phenylpropionate are obtained in the form of a white foam.

To a solution of 400 mg of 4-acetoxy-2α-benzoyloxy-5β,20-epoxy-1β,10β-dihydroxy-7β,8β-methylene-9-oxo-19-nor-11-taxen-13α-yl (2R,3S)-3-amino-2-hydroxy-3-phenylpropionate in 1 cm³ of dichloromethane, kept under an argon atmosphere, are added 60 mg of sodium hydrogen carbonate and then, dropwise, at a temperature close to 20° C., a solution of 0.16 g of di-tert-butyl dicarbonate in 1 cm³ of dichloromethane. The solution obtained is stirred for 64 hours at a temperature close to 20° C. and then supplemented with a mixture of 5 cm³ of distilled water and 10 cm³ of dichloromethane. The organic phase is washed with three times 2 cm³ of distilled water. The organic phase is dried over magnesium sulphate, filtered and then concentrated to dryness under reduced pressure (2.7 kPa) at 40° C. 317 mg of a white foam are thus obtained which are purified by chromatography on 30 g of silica (0.063-0.2 mm) contained in a column 3 cm in diameter, eluting with a dichloromethane-methanol mixture (95-5 by volume) and collecting 5 cm³ fractions. The fractions containing only the desired product are pooled and concentrated to dryness under reduced pressure (0.27 kPa) at 40° C. for 2 hours. 161 mg of 4-acetoxy-2α-benzoyloxy-5β,20-epoxy-1β,10β-dihydroxy-7β,8β-methylene-9-oxo-19-nor-11-taxen-13α-yl (2R, 3S)-3-tert-butoxycarbonylamino-2-hydroxy-3-phenylpropionate are thus obtained in the form of a white foam whose characteristics are the following:

specific rotation: $[\alpha]_D^{20}$=−17° (c=0.482; methanol)

proton NMR spectrum: (400 MHz; CDCl$_3$; temperature of 323 K; δ in ppm; coupling constants J in Hz):1.21 (s, 3H:—C$\underline{H}_3$ 16 or 17); 1.28 (s, 3H:—C$\underline{H}_3$ 16 or 17); 1.34 [s, 9H:—C(C$\underline{H}_3$)$_3$]; from 1.30 to 1.50 (mt, 1H:—$\underline{H}$7); 1.80 and 2.36 (2 mt, 1H each:—C$\underline{H}_2$— of cyclopropane); 1.88 (s, 3H:—C$\underline{H}_3$ 18); 2.13 [mt, 1H:—(CH)—$\underline{H}$6]; 2.26 [dd, 1H, J=15 to 8.5:—(CH)—$\underline{H}$ 14]; 2.35 (s, 3H:—COC$\underline{H}_3$); from 2.35 to 2.50 [mt, 2H:—(CH) —$\underline{H}$ 14 and —(CH)—$\underline{H}$ 6]; 3.21 (d, 1H, J=4:—O$\underline{H}$ 2'); 4.08 [d, 1H, J=8:—(CH)—$\underline{H}$ 20]; 4.16 (d, 1H, J=7: —$\underline{H}$ 3); 4.18 (s, 1H, —O$\underline{H}$ 10); 4.31 [d, 1H, J=8:—(CH)—$\underline{H}$ 20]:4.61 (dd, 1H, J=4 and 2:—$\underline{H}$ 2'); 4.74 (d, 1H, J=4:—$\underline{H}$ 5); 5.00 (s, 1$\underline{H}$:—$\underline{H}$ 10); 5.26 (dd, 1H, J=9 and 2:—$\underline{H}$ 3'); 5.33 (d, 1H, J=9:—N$\underline{H}$ 3'); 5.69 (d, 1H, J - 7:—$\underline{H}$ 2); 6.29 (d, 1H, J=8.5:—$\underline{H}$ 13); from 7.30 to 7.50 [mt, 5H:—C$_6$H$_5$ in 3' (—$\underline{H}$ 2 to —$\underline{H}$ 6); 7.51 [t, 2H, J=7.5:—OCOC$_6$H$_5$ (—$\underline{H}$ 3 to $\underline{H}$ 5)]; 7.60 [t, 1H, J=7.5:—OCOC$_6$H$_5$ (—$\underline{H}$ 4)]; 8.14 [d, 2H, J=7.5:—OCOC$_6$H$_5$ (—$\underline{H}$ 2 and $\underline{H}$ 6)].

The 4-acetoxy-2α-benzoyloxy-5β, 20-epoxy-1, 10β-dihydroxy-7β, 8β-methylene-9-oxo-19-nor-11-taxen-13α-yl (4S, 5R)-3-tert-butoxycarbonyl-2,2-dimethyl-4-phenyl-5-oxazolidinecarboxylate can be prepared in the following manner:

To a solution of 2.5 g of 4-acetoxy-2α-benzoyloxy-5β, 20-epoxy-1β, 10β-dihydroxy-9-oxo-7β-trifluoromethanesulphonate-11-taxen-13α-yl (4S, 5R)-3-tert-butoxycarbonyl-2, 2-dimethyl-4-phenyl-5-oxazolidinecarboxylate in 25 cm$^3$ of anhydrous acetonitrile and 3 cm$^3$ of anhydrous tetrahydrofuran, kept under an argon atmosphere, are added 2.5 g of sodium azide. The reaction mixture is heated for 2 hours, with stirring and under an argon atmosphere at a temperature close to 80° C., then cooled to a temperature close to 20° C. and supplemented with 30 cm$^3$ of distilled water. The aqueous phase is separated by decantation and then extracted with 20 cm$^3$ of dichloromethane. The combined organic phases are dried over magnesium sulphate, filtered and then concentrated to dryness under reduced pressure (2.7 kPa) at 40° C. 2.44 g of a yellow foam are thus obtained which are purified by chromatography on 300 g of silica (0.063–0.2 mm) contained in a column 8 cm in diameter, eluting with a dichloromethane-ethyl acetate mixture (90-10 by volume) and collecting 60 cm$^3$ fractions. Fractions 47 to 70 are pooled and concentrated to dryness under reduced pressure (0.27 kPa) at 40° C. for 2 hours. 2.01 g of 4-acetoxy-2α-benzoyloxy-5β,20-epoxy-1β, 10β-dihydroxy-7β,8β-methylene-9-oxo-19-nor-11-taxen-13α-yl (4S, 5R)-3-tert-butoxycarbonyl-2,2-dimethyl-4-phenyl-5-oxazolidinecarboxylate are thus obtained in the form of a white foam.

The 4-acetoxy-2α-benzoyloxy-5β, 20-epoxy-1β,10β-dihydroxy-9-oxo-7β-trifluoromethanesulphonate-11-taxen-13α-yl (4S,5R)-3-tert-butoxycarbonyl-2,2-dimethyl-4-phenyl-5-oxazolidinecarboxylate can be prepared in the following manner:

To a solution of 2.86 g of 4-acetoxy-2α-benzoyloxy-5β, 20-epoxy-1β,7β,10β-trihydroxy-9-oxo-11-taxen-13α-yl (4S,5R)-3-tert-butoxycarbonyl-2,2-dimethyl-4-phenyl-5-oxazolidinecarboxylate in 29 cm$^3$ of anhydrous dichloromethane, kept under an argon atmosphere, are added 0.955 cm$^3$ of pyridine and 50 mg of powdered activated 4Å molecular sieve. The reaction mixture is cooled to a temperature close to −35° C., slowly supplemented with 0.85 cm$^3$ of trifluoromethanesulphonic anhydride, stirred at a temperature close to −5° C. for 15 minutes and supplemented with 10 cm$^3$ of distilled water. After filtration on sintered glass provided with celite and rinsing off the sintered glass with 3 times 10 cm$^3$ of a methanol-dichloromethane mixture (10-90 by volume), the aqueous phase is separated after settling has taken place and extracted with twice 10 cm$^3$ of dichloromethane. The organic phases are pooled, dried over magnesium sulphate, filtered and then concentrated to dryness under reduced pressure (2.7 kPa) at 40° C. 3.87 g of a white foam are obtained which are purified by chromatography on 400 g of silica (0.063–0.2 mm) contained in a column 10 cm in diameter, eluting with a dichloromethane-ethyl acetate gradient (from 97.5-2.5 to 90-10 by volume) and collecting 80 cm$^3$ fractions. The fractions containing only the desired product are pooled and concentrated to dryness under reduced pressure (0.27 kPa) at 40° C. for 2 hours. 3.0 g of 4-acetoxy-2α-benzoyloxy-5β, 20-epoxy-1β,10β-dihydroxy-9-oxo-7β-trifluoromethanesulphonate-11-taxen-13α-yl(4S, 5R)-3-tert-butoxycarbonyl-2,2-dimethyl-4-phenyl-5-oxazolidinecarboxylate are thus obtained in the form of a white foam.

The 4-acetoxy-2α-benzoyloxy-5β,20-epoxy-1β,7β,10β-trihydroxy-9-oxo-11-taxen-13α-yl (4S, 5R)-3-tert-butoxycarbonyl-2,2-dimethyl-4-phenyl-5-oxazolidinecarboxylate can be prepared in the following manner:

A solution of 24.35 g of 4-acetoxy-2α-benzoyloxy-5β, 20-epoxy-9-oxo-7β,10β-[bis(2,2,2-trichloroethoxy)carbonyloxy]-1β-hydroxy-11-taxen-13α-yl(4S,5R)-3-tert-butoxycarbonyl-2,2-dimethyl-4-phenyl-5-oxazolidinecarboxylate in a mixture of 130 cm$^3$ of ethyl acetate and 46.5 cm$^3$ of acetic acid is heated, with stirring and under an argon atmosphere up to a temperature close to 60° C. and then supplemented with 40 g of zinc powder. The reaction mixture is then stirred for 30 minutes at 60° C. and then cooled to a temperature close to 20° C. and filtered on sintered glass provided with celite. The sintered glass is washed with 100 cm$^3$ of a methanol-dichloromethane mixture (20–80 by volume); the filtrates are pooled and then concentrated to dryness under reduced pressure (0.27 kPa) at a temperature close to 40° C.

The residue is supplemented with 500 cm$^3$ of dichloromethane. The organic phase is washed with twice 50 cm$^3$ of a saturated aqueous sodium hydrogen carbonate solution and then with 50 cm$^3$ of distilled water. The aqueous phases obtained after settling has taken place and pooled are extracted with twice 30 cm$^3$ of dichloromethane. The organic phases are pooled, dried over magnesium sulphate, filtered and then concentrated to dryness under reduced pressure (2.7 kPa) at 40° C. 19.7 g of a white foam are obtained which are purified by chromatography on 800 g of silica (0.063-0.2 mm) contained in a column 10 cm in diameter, eluting with a dichloromethane-methanol gradient (from 100-0 to 97-3 by volume) and collecting 80 cm$^3$ fractions. The fractions containing only the desired product are pooled and concentrated to dryness under reduced pressure (0.27 kPa) at 40° C. for 2 hours. 16.53 g of 4-acetoxy-2α-benzoyloxy-5β,20-epoxy-1β,7β, 10β-trihydroxy-9-oxo-11-taxen-13α-yl (4S,5R)-3-tert-butoxycarbonyl-2,2-dimethyl-4-phenyl-5-oxazolidinecarboxylate in the form of a white foam.

The 4-acetoxy-2α-benzoyloxy-5β,20-epoxy-9-oxo-7β, 10β-[bis(2,2,2-trichloroethoxy)carbonyloxy]-1β-hydroxy-11-taxen-13α-yl (4S,5R)-3-tert-butoxycarbonyl-2,2-dimethyl-4-phenyl-5-oxazolidinecarboxylate can be prepared according to the method described in international application PCT WO 9209589.

Example 2

To a solution of 550 mg of 4α,10β-diacetoxy-2α-benzoyloxy-5β,20-epoxy-1β-hydroxy-7β,8β-methylene-9-oxo-19-nor-11-taxen-13α-yl (2R,3S)-3-amino-2-hydroxy- 3-phenylpropionate are added 45 cm³ of distilled water, 45 cm³ of a saturated aqueous sodium hydrogen carbonate solution and then, dropwise, at a temperature close to 20° C., 0.096 cm³ of benzoyl chloride. The mixture obtained is stirred for 10 minutes at a temperature close to 20° C. After settling has taken place, the aqueous phase is extracted with twice 30 cm³ of ethyl acetate. The combined organic phases are dried over magnesium sulphate, filtered and then concentrated to dryness under reduced pressure (2.7 kPa) at 40° C. 670 mg of a white foam are thus obtained which are purified by chromatography at atmospheric pressure on 50 g of silica (0.063–0.2 mm) contained in a column 2.5 cm in diameter, eluting with a methanol-dichloromethane mixture (1–99 then 2.5–97.5 by volume) and collecting 10 cm³ fractions. The fractions containing only the desired product are pooled and concentrated to dryness under reduced pressure (2.7 kPa) at 40° C. 610 mg of a white foam are thus obtained. A sample of 300 mg is purified by preparative chromatography on 12 thin-layer silica plates (Kieselgel 60F254, Merck; thickness 0.25 mm), eluting with a methanol-dichloromethane mixture (3–97 by volume). After elution of the zone corresponding to the main product with a methanol-dichloromethane mixture (10–90 by volume) and then evaporation of the solvents under reduced pressure (0.27 kPa) at a temperature close to 40° C., 155.2 mg of 4α,10β-diacetoxy-2α-benzoyloxy-5β,20-epoxy-1β-hydroxy-7β,8β-methylene-9-oxo-19-nor-11-taxen-13α-yl (2R,3S)-3-benzoylamino-2-hydroxy-3-phenylpropionate are obtained in the form of a white foam whose characteristics are the following:

specific rotation: $[\alpha]_D^{20}=-30.5°$ (c=0.491; methanol)

proton NMR spectrum: (300 MHz; CDCl₃; δ in ppm; coupling constants J in Hz):1.27 (s, 3H: —C$\underline{H}_3$ 16 or 17); 1.30 (s, 3H: —C$\underline{H}_3$ 16 or 17); 1.40 (mt, 1H: —$\underline{H}$7); 1.62 and 2.25 (q and m, 1H each: C$\underline{H}_2$— of cyclopropane); 1.85 (s, 3H: —C$\underline{H}_3$ 18); 1.96 (s, 1H: —O$\underline{H}$ in 1); 2.05 and 2.48 (d and m, 1H each: —C$\underline{H}_2$— in 6); 2.24 (s, 3H: —COC$\underline{H}_3$ in 10); 2.28 and 2.50 (m, 1H each: —C$\underline{H}_2$ in 14); 2.45 (s, 3H: —COC$\underline{H}_3$ in 4); 3.52 (d, 1H: —O$\underline{H}$ in 2'); 4.10 and 4.35 (d, 1H each: —C$\underline{H}_2$ in 20); 4.11 (d, 1H: —$\underline{H}$3); 4.77 (broad d, 1H: —$\underline{H}$5); 4.82 (dd, 1H: —$\underline{H}$2'); 5.70 (d, 1H: —$\underline{H}$ in 2); 5.84 (dd, 1H: —$\underline{H}$3'); 6.30 (broad t, 1H: —$\underline{H}$13); 6.36 (s, 1H: —$\underline{H}$10); 7.00 (d, 1H: —CON$\underline{H}$—); from 7.35 to 8.30 (m, 15H: —C₆$\underline{H}_5$ in 3', —OCOC₆$\underline{H}_5$ and NHCOC₆$\underline{H}_5$).

The 4α,10β-diacetoxy-2α-benzoyloxy-5β,2β-epoxy-1β-hydroxy-7β,8β-methylene-9-oxo-19-nor-11-taxen-13α-yl (2R, 3S)-3-amino-2-hydroxy-3-phenylpropionate can be prepared by carrying out the procedure under the conditions described in Example 1 for the preparation of 4-acetoxy-2α-benzoyloxy-5β,20-epoxy-1β,10β-dihydroxy-7β,8β-methylene-9-oxo-19-nor-11-taxen-13α-yl (2R,3S)-3-amino-2-hydroxy-3-phenylpropionate. Thus, starting with 1.6 g of 4α,10β-diacetoxy-2α-benzoyloxy-5β,20-epoxy-1β-hydroxy-7β,8β-methylene-9-oxo-19-nor-11-taxen-13α-yl (4S,5R)-3-tert-butoxycarbonyl-2,2-dimethyl-4-phenyl-5-oxazolidincarboxylate, 1.14 g of 4α,10β-diacetoxy-2α-benzoyloxy-5β,20-epoxy-1β-hydroxy-7β,8β-methylene-9-oxo-19-nor-11-taxen-13α-yl are obtained in the form of a white foam.

The 4α,10β-diacetoxy-2α-benzoyloxy-5β,20-epoxy-1β-hydroxy-7β,8β-methylene-9-oxo-19-nor-11-taxen-13α-yl (4S,5R)-3-tert-butoxycarbonyl-2,2-dimethyl-4-phenyl-5-oxazolidincarboxylate can be prepared under the conditions described in Example 1 for the preparation of 4α-acetoxy-2α-benzoyloxy-5β,20-epoxy-1β,10β-dihydroxy-7β,8β-methylene-9-oxo-19-nor-11-taxen-13α-yl (4S,5R)-3-tert-butoxycarbonyl-2,2-dimethyl-4-phenyl-5-oxazolidinecarboxylate. Thus, starting with 2.2 g of 4α,10β-diacetoxy-2α-benzoyloxy-5β,20-epoxy-1β-hydroxy-9-oxo-7β-trifluoromethanesulphonate-11-taxen-13α-yl (4S,5R)-3-tert-butoxycarbonyl-2,2-dimethyl-4-phenyl-5-oxazolidincarboxylate, 1.62 g of 4α,10β-diacetoxy-2α-benzoyloxy-5β,20-epoxy-1β-hydroxy-7β,8β-methylene-9-oxo-19-nor-11-taxen-13α-yl (4S,5R)-3-tert-butoxycarbonyl-2,2-dimethyl-4-phenyl-5-oxazolidincarboxylate are obtained in the form of a white foam.

The 4α,10β-diacetoxy-2α-benzoyloxy-5β,20-epoxy-1β-hydroxy-9-oxo-7β-trifluoromethanesulphonate-11-taxen-13α-yl (4S,5R)-3-tert-butoxycarbonyl-2,2-dimethyl-4-phenyl-5-oxazolidincarboxylate can be prepared under the conditions described in Example 1 for the preparation of 4α-acetoxy-2α-benzoyloxy-5β,20-epoxy-1β,10β-dihydroxy-9-oxo-7β-trifluoromethanesulphonate-19-nor-11-taxen-13α-yl (4S,5R)-3-tert-butoxycarbonyl-2,2-dimethyl-4-phenyl-5-oxazolidincarboxylate. Thus, starting with 2.4 g of 4α,10β-diacetoxy-2α-benzoyloxy-5β,20-epoxy-1β,7β-dihydroxy-9-oxo-11-taxen-13α-yl (4S,6R)-3-tert-butoxycarbonyl-2,2-dimethyl-4-phenyl-5-oxazolidincarboxylate, 2.46 g of 4α,10β-diacetoxy-2α-benzoyloxy-5β,20-epoxy-1β-hydroxy-9-oxo-7β-trifluoromethanesulphonate-11-taxen-13α-yl (4S,5R)-3-tert-butoxycarbonyl-2,2-dimethyl-4-phenyl-5-oxazolidincarboxylate are obtained in the form of a white foam.

The 4α,10β-diacetoxy-2α-benzoyloxy-5β,20-epoxy-1β,7β-dihydroxy-9-oxo-11-taxen-13α-yl (4S,5R)-3-tert-butoxycarbonyl-2,2-dimethyl-4-phenyl-5-oxazolidincarboxylate can be prepared under the conditions described in International Application PCT WO 9209589.

Example 3

To a solution of 550 mg of 4α,10β-diacetoxy-2α-benzoyloxy-5β,20-epoxy-1β-hydroxy-7β,8β-methylene-9-oxo-19-nor-11-taxen-13α-yl (2R,3S)-3-amino-2-hydroxy-3-phenylpropionate in 1 cm³ of dichloromethane, kept under an argon atmosphere, are added 76 mg of sodium hydrogen carbonate and then, dropwise, at a temperature close to 20° C., a solution of 197 mg of di-tert-butyl dicarbonate in 1 cm³ of dichloromethane. The solution obtained is stirred for 15 hours at a temperature close to 20° C. and then supplemented with a mixture of 5 cm³ of distilled water and 10 cm³ of dichloromethane. The aqueous phase is extracted with 5 cm³ of dichloromethane. The combined organic phases are dried over magnesium sulphate, filtered and then concentrated to dryness under reduced pressure (2.7 kPa) at 40° C. 780 mg of a white foam are thus obtained which are purified by chromatography at atmospheric pressure on 50 g of silica (0.063–0.2 mm) contained in a column 2.5 cm in diameter, eluting with a methanol-dichloromethane mixture (1-99 then 2.5-97.5 by volume) and collecting 10 cm³ fractions. The fractions containing only the desired product are pooled and concentrated to dryness under reduced pressure (2.7 kPa) at 40° C. 660 mg of a white foam are thus obtained. A sample of 300 mg is purified by preparative chromatography on 12 thin-layer silica plates (Kieselgel 60F254, Merck; thickness 0.25 mm), eluting with a methanol-dichloromethane mixture (4-96 by volume). After elution of the zone corresponding to the main product with a methanol-dichloromethane mixture (10-90 by volume) and then evaporation of the solvents under reduced pressure (0.27 kPa) at a temperature close to 40° C., 159.7 mg of 4α,10β-diacetoxy-2α-benzoyloxy-5β, 20-epoxy-1-hydroxy-7β,8β-methylene-9-oxo-19-nor-11-taxen-13α-yl (2R,3S)-3-tert-butoxycarbonylamino-2- hydroxy-3-phenylpropionate are obtained in the form of a white foam whose characteristics are the following:

specific rotation: $[\alpha]_D^{20} = -34°$ (c=0.564; methanol)

proton NMR spectrum: (400 MHz; CDCl$_3$; δ in ppm; coupling constants J in Hz): 1.28 (s, 3H: —C$\underline{H}_3$ 16 or 17); 1.30 [s, 9H: —C(C$\underline{H}_3$)$_3$]; 1.38 (mt, 1H: —$\underline{H}$7); 1.60 (s, 3H: —C$\underline{H}_3$ 16 or 17); 1.68 and 2.25 (t and m, 1H each; C$\underline{H}_3$— of cyclopropane); 1.85 (s, 3H: —CH$_3$ 18); 2.10 and 2.45 (d and td, 1H each: —C$\underline{H}_3$— in 6); 2.23 (s, 3H: —COC$\underline{H}_3$ in 10); 2.22 and 2.40 (m, 1H each: —C$\underline{H}_2$— in 14); 2.40 (s, 3H: —COC$\underline{H}_3$ in 4); 3.28 (d, 1H: —O$\underline{H}$ in 2'); 4.05 and 4.22 (d, 1H each: —C$\underline{H}_2$— in 20); 4.10 (d, 1H: —$\underline{H}$3); 4.62 (broad s, 1H: —$\underline{H}$2'); 4.73 (d, 1H: —$\underline{H}$5); 5.29 (broad d, 1H: —$\underline{H}$3'); 5.37 (d, 1H: —CON$\underline{H}$—); 5.67 (d, 1H: —H in 2); 6.28 (broad t, 1H: —$\underline{H}$13); 6.33 (s, 1H: —$\underline{H}$10); from 7.30 to 7.45 (mt, 5H: —C$_6$H$_5$ in 3'); 7.51 [t, 2H: —OCOC$_6$H$_5$ (—$\underline{H}$3 and —$\underline{H}$5)]; 7.61 [t, 1H: —OCOC$_6$H$_5$ (—$\underline{H}$4)]; 8.17 [d, 2H: —OCOC$_6$H$_5$ (—$\underline{H}$2 and —$\underline{H}$6)].

Example 4

To a solution of 100 mg of 10-deacetyl-baccatin III in a mixture of 3 cm$^3$ of tetrahydrofuran and 0.05 cm$^3$ of pyridine cooled to a temperature close to −78° C. and kept under an argon atmosphere, is added, dropwise, 0.09 cm$^3$ of trifluoro-methanesulphonic anhydride. The temperature is allowed to rise slowly to a temperature close to 0° C. over approximately one hour, then up to a temperature close to 20° C. over approximately one hour. After 2 hours at a temperature close to 20° C., 200 mg of tetrabutylammonium iodide are added, then the solution is heated at the boiling temperature of the solvent for 15 hours. After cooling to a temperature close to 20° C., 10 cm$^3$ of ethyl acetate and then 1 cm$^3$ of distilled water are added. After separation after settling has taken place, the organic phase is dried over magnesium sulphate, filtered and concentrated to dryness under reduced pressure (2.7 kPa) at 40° C. 116 mg of a yellow oil are thus obtained which are purified by chromatography at atmospheric pressure on 30 g of silica (0.063–0.2 mm) contained in a column 2.5 cm in diameter, eluting with an ethyl acetate-dichloromethane mixture, with an elution gradient from 0–100 to 80–20 by volume. The fractions containing the desired product are pooled and concentrated to dryness under reduced pressure (0.27 kPa) at 40° C. 10.3 mg of 10-deacetyl-7β,8β-methylene-19-norbaccatin III are thus obtained in the form of a white foam whose characteristics are the following:

proton NMR spectrum: (400 MHz; CDCl$_3$; δ in ppm; coupling constants J in Hz): 1.14 (s, 3H: —C$\underline{H}_3$ in 16 or 17); 1.42 (mt, 1H: —$\underline{H}$ in 7); 1.76 and 2.31 (t and m, 1H each; C$\underline{H}_2$ of cyclopropane); 2.07 (s, 3H; —C$\underline{H}_3$ in 18); 2.15 and 2.50 (broad d and td, 1H each: C$\underline{H}_2$— in 6); 2.30 (s, 3H: —COC$\underline{H}_3$ in 4); 2.28 and 2.35 (m, 1H each: —C$\underline{H}_2$ in 14); 4.11 and 4.37 (d, 1H each: —C$\underline{H}_2$ in 20); 4.28 (d, 1H: —$\underline{H}$3 in 3); 4.79 (d, 1H: —$\underline{H}$ in 5); 4.88 (broad t, 1H: —$\underline{H}$ in 13); 5.09 (s, 1H: —$\underline{H}$ in 10); 5.66 (d, 1H: —$\underline{H}$ in 2); 7.51 [t, 2H: —OCOC$_6$H$_5$ (—$\underline{H}$ in 3 and 5)]; 7.61 [t, 1H: —OCOC$_6$H$_5$ (—$\underline{H}$ in 4)]; 8.17 [d, 2H: —OCOC$_6$H$_5$ (—$\underline{H}$ in 2 and 6)]. $^{13}$C NMR spectrum: (100 MHz; CDCl$_3$; δ in ppm; uncoupled; s=singlet, d=doublet; t=triplet; q=quadruplet): 15 (q, C18); 16.5 (t, C19); 20 and 27 (g, C16 and C17); 22.5 (q, —CO$\underline{C}$H$_3$); 26.5 (t, C6); 33 (d, C7); 35 (s, C8); 39 (d, C3); 39.5 (t, C14); 43 (s, C15); 68 (d, C13); 76 (t, C20); 76.2 (d, C10); 79.5 (s, C1); 80 (s, C4); 81 (d, C2); 85 (d, C5); 129 (d, C2: —OCOC$_6$H$_5$); 130 (s, Cl of —OCOC$_6$H$_5$); 130.5 (d, C3 of —OCOC$_6$H$_5$); 134 (d, C4 of —OCOC$_6$H$_5$); 136 (s, C11); 143 (s, C12); 168 (s, —O$\underline{C}$OC$_6$H$_5$); 171 (s, —$\underline{C}$OCH$_3$); 210 (s, C9).

The new products of general formula (I) manifest a significant inhibitory activity with respect to abnormal cell proliferation and possess therapeutic properties which permit the treatment of patients having pathological conditions associated with abnormal cell proliferation. The pathological conditions include the abnormal cell proliferation of malignant or nonmalignant cells of various tissues and/or organs, comprising, with no limitation being implied, muscle, bone or connective tissues, the skin, brain, lungs, sex organs, the lymphatic or renal systems, mammary or blood cells, liver, the digestive tract, pancreas and thyroid or adrenal glands. These pathological conditions can also include psoriasis, solid tumours, cancers of the ovary, breast, brain, prostate, colon, stomach, kidney or testicles, Kaposi's sarcoma, cholangioma, chorioma, neuroblastoma, Wilms' tumour, Hodgkin's disease, melanomas, multiple myelomas, lymphatic leukemias and acute or chronic granulocytic lymphomas. The new products according to the invention are particularly useful for the treatment of cancer of the ovary. The products according to the invention can be used to prevent or retard the appearance or reappearance of the pathological conditions or to treat these pathological conditions.

The products according to the invention can be administered to a patient in various forms adapted to the chosen route of administration which is preferably the parenteral route. Parenteral administration comprises intravenous, intraperitoneal, intramuscular or subcutaneous administrations. Intraperitoneal or intravenous administration is more particularly preferred.

The present invention also comprises pharmaceutical compositions containing at least one product of general formula (I) in a sufficient quantity adapted to use in human or veterinary therapy. The compositions can be prepared according to the customary methods, using one or more pharmaceutically acceptable adjuvants, carriers or excipients. Suitable carriers include diluents, sterile aqueous media and various nontoxic solvents. Preferably, the compositions are provided in the form of aqueous solutions or suspensions, of injectable solutions which may contain emulsifying agents, colorants, preservatives or stabilizers.

The choice of adjuvants or excipients may be determined by the solubility and the chemical properties of the product, the particular mode of administration and good pharmaceutical practice.

For parenteral administration, aqueous or nonaqueous sterile solutions or suspensions are used. For the preparation of nonaqueous solutions or suspensions, natural vegetable oils such as olive oil, sesame oil or paraffin oil or injectable organic esters such as ethyl oleate can be used. The aqueous sterile solutions may consist of a solution of a pharmaceutically acceptable salt in solution in water. The aqueous solutions are suitable for intravenous administration insofar as the pH is appropriately adjusted and isotonicity is achieved, for example, with a sufficient quantity of sodium chloride or glucose. The sterilization can be performed by heating or by any other means which does not adversely affect the composition.

It is clearly understood that all the products entering into the compositions according to the invention should be substantially pure and nontoxic for the quantities used.

The compositions may contain at least 0.01% of therapeutically active product. The quantity of active product in a composition is such that a suitable dosage can be prescribed. Preferably, the compositions are prepared such that a single dose contains about 0.01 to 1000 mg of active product for parenteral administration.

The therapeutic treatment can be performed concurrently with other therapeutic treatments including antineoplastic drugs, monoclonal antibodies, immunotherapies or radiotherapies or biological response modifiers. The response modifiers include, with no limitation being implied, lymphokines and cytokines such as interleukins, interferons (α, β or δ) and TNF. Other chemotherapeutic agents which are useful in the treatment of disorders caused by abnormal proliferation of cells include, with no limitation being implied, alkylating agents like nitrogen mustards such as mechloretamine, cyclophosphamide, melphalan and chlorambucil, alkyl sulphonates such as busulfan, nitrosoureas such as carmustine, lomustine, semustine and streptozocin, triazenes such as dacarbazine, antimetabolites such as folic acid analogues like methotrexate, pyrimidine analogues such as fluorouracil and cytarabine, purine analogues such as mercaptopurine and thioguanine, natural products like vinca alkaloids such as vinblastine, vincristine and vindesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum like cisplatin, substituted ureas like hydroxyurea, methylhydrazine derivatives such as procarbazine, adrenocortical suppressants such as mitotane and aminoglutethymide, hormones and antagonists such as adrenocorticosteroids such as prednisone, progestins such as hydroxyprogesterone caproate, methoxyprogesterone acetate and megestrol acetate, oestrogens such as diethylstilbestrol and ethynylestradiol, antioestrogens such as tamoxifen, and androgens such as testosterone propionate and fluoroxymesterone.

The doses used for carrying out the methods according to the invention are those which permit a prophylactic treatment or a maximum therapeutic response. The doses vary according to the form of administration, the particular product selected and the characteristics specific to the subject to be treated. In general, the doses are those which are therapeutically effective for the treatment of disorders caused by abnormal cell proliferation. The products according to the invention can be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly higher doses will be administered until an optimum effect is obtained. For other patients, it may be necessary to administer maintenance doses 1 to 8 times per day, preferably 1 to 4 times according to the physiological needs of the patient considered. It is also possible that for certain patients it may be necessary to use only one to two daily administrations.

In man, the doses are generally range from 0.01 to 200 mg/kg. For intraperitoneal administration, the doses will generally range from 0.1 to 100 mg/kg and, preferably, from 0.5 to 50 mg/kg and, still more specifically, from 1 to 10 mg/kg. For intravenous administration, the doses are generally range from 0.1 to 50 mg/kg and, preferably, from 0.1 to 5 mg/kg and, still more specifically, from 1 to 2 mg/kg. It is understood that, in order to choose the most appropriate dosage, account should be taken of the route of administration, the patient's weight, his general state of health, his age and all factors which may influence the efficacy of the treatment.

The following example is generally illustrative.

Example 5

40 mg of the product obtained in Example 1 are dissolved in 1 cm³ of Emulphor EL 620 and 1 cm³ of ethanol and then the solution is diluted by addition of 18 cm³ of physiological saline.

The composition is administered by perfusion for 1 hour by introduction into physiological saline.

Example 6

To a solution of 1.2 g of 4-acetoxy-2α-benzoyloxy-5β, 20-epoxy-1-hydroxy-10β-methoxyacetoxy-7β-trifluoromethanesulphonyloxy-9-oxo-11-taxen-13α-yl (2R, 3S)-3-tert-butoxycarbonylamino-2-hydroxy-(3-thienyl) propionate in a mixture of 15 cm³ of anhydrous acetonitrile and 1.5 cm³ of anhydrous tetrahydrofuran, under argon atmosphere, are added 0.6 g of powdered 4 Å molecular sieve and 1.8 g of sodium chloride. The reaction mixture is stirred at 20° C. for 30 minutes, then heated at the boiling temperature of the solvent for 2 hours. After cooling at 20° C., 50 cm³ of dichloromethane are added and the reaction mixture is filtered on a sintered glass filter. The filter is washed with twice 20 cm³ of dichloromethane and the pooled filtrates are washed with twice 20 cm³ of water, dried over sodium sulphate, filtered and concentrated at 40° C. under reduced pressure (2.7 kPa). 925 mg of a white amorphous solid are obtained which are purified by chromatography on 100 g silica gel (0.063–0.2 mm) contained in a column 3 cm in diameter, eluting with a dichloromethane-methanol mixture (99-10 by volume)and collecting 25 cm³ fractions. Fractions 16 and 26 are pooled and concentrated to dryness under reduced pressure (2.7 kPa) at 40° C. for 16 hours. 217 mg of 4-acetoxy-2α-benzoyloxy-5β,20-epoxy-1-hydroxy-10β-methoxyacetoxy-7β,8β-methylene-9-oxo-19-nor 11-taxen-13α-yl (2R,3S)-3-tert-butoxycarbonylamino-2-hydroxy-(3-thienyl) propionate are thus obtained in the form of a white amorphous solid whose characteristics are the following:

specific rotation: $[\alpha]_D^{20}=-28$ (c=0.37; methanol)

proton NMR spectrum (400 MHz; CDCl₃; δ in ppm; coupling constants J in Hz): 1.25 (s, 3H: CH₃); 1.27 (s, 3H: CH₃); 1.31 (s, 9H: C(CH₃)₃); 1.40 (m, 1H: H 7); 1.69, 2.20 to 2.35 (2 m, 1H each: CH₂ 19); 1.84 (s, 1H : OH 1); 1.87 (s, 3H : CH₃); 2.11, 2.35 to 2.50 (respectively : broad d, J=16, and m, 1H each: CH₂ 6); 2.20 to 2.50 (m, 2H : CH₂ 14); 2.37 (s, 3H : COCH₃); 3.30 (m, 1H: OH 2'); 3.52 (s, 3H: OCH₃); 4.04 and 4.30 (2d,J=9, 1H each: CH₂ 20); 4.10 (d,J=7, 1H: H 3); 4.21 (AB limit, J=16, 2H: OCOCH₂O); 4.62 (m, 1H: H 2'); 4.72 (m, 1H: H 5); 5.20 (d,J=10, 1H: CONH); 5.34 (m, 1H: H 3'); 5.68 (d,J =7, 1H: H 2); 6.26 (broad t, J=9, 1H: H 13); 6.41 (s, 1H: H 10); 7.10 (d,J=4, H-4 thienyl); 7.28 (m, 1H: H-2 thienyl); 7.37 (dd, J=4 and 3.5, 1H: H-5 thienyl); 7.51 (t, J=7.5, 2H : OCOC₆H₅ H-meta); 7.61 (t, J=7.5, 1H: OCOC₆H₅ H-para); 8.15 (d, J=7.5, 2H: OCOC₆H₅ H-ortho).

4-Acetoxy-2α-benzoyloxy-5β,20-epoxy-1-hydroxy-10β-methoxyacetoxy-7β-trifluoromethanesulphonyloxy-9-oxo-11-taxen-13α-yl (2R,3S)-3-tert-butoxycarbonylamino-2-(1-ethoxyethoxy)-3-(3-thienyl) propionate can be prepared in the following way:

To a solution of 1.12 g of 4-acetoxy-2α-benzoyloxy-5β, 20-epoxy-1,13α-dihydroxy-10β-methoxyacetoxy-7β-trifluoromethanesulphonyloxy-9-oxo-11-taxene in 75 cm³ of anhydrous tetrahydrofuran, under argon atmosphere, are added 0.80 g of (3R,4S)-1-(tert-butoxycarbonyl)-3-(1-ethoxyethoxy)-4-(3-thienyl)-2-azetidinone at 20° C. The reaction mixture is cooled at −30° C. and 2 cm³ of a 2M solution of sodium bis(trimethylsilyl)amide in tetrahydrofuran are added dropwise while the temperature is maintained at −30° C. The reaction mixture is cooled at −30° C. for 30 minutes, then warmed at 20° C. A mixture of 50 cm³ of a saturated aqueous ammonium chloride solution and 50 cm³ of water is added. The mixture is extracted with twice 150 cm³ dichloromethane. The organic phases are pooled, washed with 3 times 75 cm³ water, dried over sodium sulphate, filtered and concentrated to dryness under reduced pressure (2.7 kPa) at 40° C. 1.75 g of a pale yellow amorphous solid are obtained which are purified by chromatography on 60 g of silica gel (0.063-0.2 mm) contained in a column 2.5 cm in diameter, eluting with a dichloromethane-methanol mixture (99-1 by volume) and collecting 25 cm³ fractions. Fractions 8 to 18 are pooled and concentrated under reduced pressure (0.27 kPa) at 40° C. 1.35 g of 4-acetoxy-2α-benzoyloxy-5β,20-epoxy-1-hydroxy-10β-methoxyacetoxy-7β-trifluoromethanephonyloxy-9-oxo-11-taxen-13α-yl (2R,3S)-3-tert-butoxycarbonylamino-2-(1-ethoxyethoxy)-3-(3-thienyl) propionate are obtained in the form of a white amorphous solid.

4-Acetoxy-2α-benzoyloxy-5β,20-epoxy-1,13α-dihydroxy-10β-methoxyacetoxy-7β-trifluoromethanesulphonyloxy-9-oxo-11-taxene can be prepared in the following manner:

To a solution of 10 g of 4-acetoxy-2α-benzoyloxy-5β,20-epoxy-1,7β,13α-trihydroxy-10β-methoxyacetoxy-9-oxo-11-taxene in a mixture of 500 cm³ of dichloromethane and 48 cm³ anhydrous pyridine, under argon atmosphere, are added dropwise 3.8 cm³ of trifluoromethanesulphonic anhydride, the temperature being maintained at 20° C. The reaction mixture is stirred at the boiling temperature of the solvent for 2 hours. After cooling to 20° C., 100 cm³ of water are added. The aqueous phase is decanted and extracted with 200 cm³ dichloromethane. The pooled organic phases are washed successively with 100 cm³ of water, 100 cm³ of a saturated aqueous sodium hydrogen carbonate solution and twice 75 cm³ of water, dried over sodium sulphate, filtered and concentrated to dryness under reduced pressure (2.7 kPa) at 40° C. 11.5 g of a white amorphous solid are obtained which are purified by chromatography on 400 g of silica gel (0.063–0.2 mm) contained in a column 4.5 cm in diameter, eluting with a dichloromethane-methanol mixture (99-1 by volume) and collecting 50 cm³ fractions. Fractions 15 to 31 are pooled and concentrated under reduced pressure (0.27 kPa) at 40° C. 7.2 g of 4-acetoxy-2α-benzoyloxy-5β,20-epoxy-1,13α-dihydroxy-10β-methoxyacetoxy-7β-trifluoromethanesulphonyloxy-9-oxo-11-taxene are obtained in the form of a white amorphous solid.

4-Acetoxy-2α-benzoyloxy-5β,20-epoxy-1,7β,13α-trihydroxy-10β-methoxyacetoxy-9-oxo-11-taxene can be prepared in the following manner:

To a solution of 11 g of 4-acetoxy-2α-benzoyloxy-5β,20-epoxy-7β-triethylsilyloxy-1,13α-dihydroxy-10β-methoxyacetoxy-9-oxo-11-taxene in 500 cm³ of anhydrous tetrahydrofuran, under argon atmosphere, are added dropwise 50 cm³ of hydrogen fluoride-pyridine, the temperature being maintained at 20° C. The reaction mixture is stirred at 20° C. for 2 hours, and supplemented with 10 cm³ of hydrogen fluoride-pyridine. The stirring is maintained then for 1 hour at 20° C. A mixture of 250 cm³ of water and 250 cm³ of dichloromethane is added. The pooled organic phases are washed successively with twice 75 cm³ of water, with twice 75 cm³ of a saturated aqueous sodium hydrogen carbonate solution and with twice 75 cm³ of water, dried over sodium sulphate, filtered and concentrated to dryness under reduced pressure (2.7 kPa) at 40° C. 10 g of 4-acetoxy-2α-benzoyloxy-5β,20-epoxy-1,7β,13α-trihydroxy-10β-methoxyacetoxy-9-oxo-11-taxene are obtained in the form of a white amorphous solid.

4-Acetoxy-2α-benzoyloxy-5β,20-epoxy-7β-triethylsilyloxy-1,13α-dihydroxy-10β-methoxyacetoxy-9-oxo-11-taxene can be prepared according to the international application PCT WO 94/07878 by condensing 4-acetoxy-2α-benzoyloxy-5β,20-epoxy-7β-triethylsilyloxy-1,10β,13α-trihydroxy-9-oxo-11-taxene with a methoxyacetyl halogenide. (3R,4S)-1-(tert-butoxycarbonyl)-3-(1-ethoxyethoxy)-4-(3-thienyl)-2-azetidinone can be prepared in the following manner:

To a solution of 10 g of (3R,4S)-3-(1-ethoxyethoxy)-4-(3-thienyl)-2-azetidinone in 400 cm³ of dichloromethane, under argon atmosphere, are added 12 cm³ of triethylamine and 0.1 g of 4-dimethylaminopyridine, and then, dropwise at 0° C., a solution of 13.5 g of di-tert-butyl dicarbonate in 100 cm³ of dichloromethane. The reaction mixture is warmed at 20° C. and maintained at 20° C. for 24 hours, and then 100 cm³ of water are added. The aqueous phase is decanted and extracted with 100 cm³ of dichloromethane. The pooled organic phases are washed twice with 50 cm³ of water, dried over sodium sulphate, filtered and concentrated to dryness under reduced pressure (2.7 kPa) at 40° C. 15 g of a white amorphous solid are obtained which are purified by chromatography on 240 g of silica gel (0.063-0.2 mm) contained in a column 4.5 cm in diameter, eluting with a dichloromethane-methanol mixture (99-1 by volume) and collecting 50 cm³ fractions. Fractions 7 to 18 are pooled and concentrated under reduced pressure (0.27 kPa) at 40° C. 12 g of (3R,4S)-1-(tert-butoxycarbonyl)-3-(1-ethoxyethoxy)-4-(3-thienyl)-2-azetidinone are obtained in the form of a white amorphous solid.

(3R,4S)-3-(1-ethoxyethoxy)-4-(3-thienyl)-2-azetidinone can be prepared in the following manner:

To a solution of 10 g of (3R,4S)-3-hydroxy-4-(3-thienyl)-2-azetidinone in 200 cm³ tetrahydrofuran, under an argon atmosphere, are added 0.3 g of pyridinium toluene-4-sulphonate, then, dropwise, at 20° C., 28.2 cm³ of ethyl vinyl ether. The reaction mixture is stirred and heated at 60° C. for 2 hours and concentrated to dryness under reduced pressure (2.7 kPa) at 40° C. 500 cm³ of ethyl acetate are added and the mixture is washed with 5 times 75 cm³ of water, dried over sodium sulphate, filtered and concentrated to dryness under reduced pressure (2.7 kPa) at 40° C. 14.5 g of a brown oil are obtained which are purified by chromatography on 240 g of silica gel (0.063–0.2 mm) contained in a column 4.5 cm in diameter, eluting with a dichloromethane-methanol mixture (99.5-0.5 by volume) and collecting 50 cm³ fractions. Fractions 13 to 21 are pooled and concentrated under reduced pressure (0.27 kPa) at 40° C. 10.2 g of (3R,4S)-3-(1-ethoxyethoxy)-4-(3-thienyl)-2-azetidinone are obtained in the form of pale yellow crystals melting at 60° C.

(3R,4S)-3-hydroxy-4-(3-thienyl)-2-azetidinone can be prepared according to the method described in international application PCT WO 94/24103.

Example 7

A solution of 470 mg of 4-acetoxy-2α-benzoyloxy-5β,20-epoxy-1-hydroxy-10β-methoxyacetoxy-7β,8β-methylene-9-oxo-19-nor-11-taxen 13α-yl (2R, 4S, 5R)-3-tert-butoxycarbonylamino-2-(4-methoxyphenyl)-4-phenyl-5-oxazolidinecarboxylate in 4.8 cm3 of a 0.1N solution of HCl in ethanol is stirred at 5° C. under an argon atmosphere for 17 hours. The reaction mixture is then diluted with a mixture of 5 cm³ of dichloromethane, 5 cm³ of a saturated aqueous sodium hydrogen carbonate solution and 2.5 cm³ of water. The aqueous phase is extracted with 5 cm3 of dichloromethane. The pooled organic phases are washed with 5 cm³ of water, dried over magnesium sulphate, filtered and concentrated to dryness under reduced pressure. 380 mg of a yellow foam are obtained which are chromatographed at atmospheric pressure on 15 g silica gel (0.063–0.2 mm) contained in a column 1.7 cm in diameter, eluting with a dichloromethane-methanol mixture (98-2 by volume). 300 mg of deprotected product are obtained which are purified by chromatography on silica gel plates (10 plates, 20×20 cm, thickness=0.5 mm), eluting with a dichloromethane-methanol mixture (95-5 by volume). 142 mg of pure 4-acetoxy-2α-benzoyloxy-5β,20-epoxy-1-hydroxy-10β-methoxyacetoxy-7β,8β-methylene-9-oxo-19-nor-11-taxen-13α-yl (2R,3S)-3-tert-butoxycarbonylamino-2-hydroxy-3-phenylpropionate are obtained in the form of a white foam whose characteristics are the following:

specific rotation: $[\alpha]^{20}_D = -35.8$ (c=0.25, methanol)

proton NMR spectrum (400 MHz, CDCl$_3$, δ in ppm, coupling constants J in Hz): 1.27 (s, 3H : CH$_3$); 1.28 (s, 3H: CH$_3$); 1.30 (s, 9H : C(CH$_3$)$_3$); 1.40 (m, 1H: H 7); 1.69 and 2.25 (2 m, 1H each: CH$_2$ 19); 1.86 (s, 1H: OH); 1.87 (s, 3H: CH$_3$); 2.13 and 2.48 (respectively: broad d and dt, J=16, J=16 and 4.5, 1H each: CH$_2$ 6); 2.23 and 2.39 (2 m, 1H each: CH$_2$ 14); 2.40 (s, 3H: COCH$_3$); 3.27 (m, 1H: OH 2'); 3.53 (s, 3H: OCH$_3$); 4.03 and 4.32 (2 d, J=9, 1H each: CH$_2$ 20); 4.10 (d,J=7, 1H: H 3); 4.22 (AB limit, J=16, OCOCH$_2$); 4.62 (m, 1H: H 2'); 4.74 (d,J=4.5, 1H: H 5); 5.29 (m, 1H: H 3'); 5.35 (d,J=10, 1H: CONH); 5.67 (d,J=7, 1H: H 2); 6.28 (broad t,J=9, 1H: H 13); 6.42 (s, 1H: H 10); 7.30 to 7.45 (m, 5H: H 3'-phenyl); 7.51 (t,J=7.5, 2H: OCOC$_6$H$_5$-meta); 7.61 (t, J=7.5, 2H: OCOC$_6$H$_5$H-para); 8.15 (t,J=7.5, 2H: OCOC$_6$H$_5$ H-ortho).

4-Acetoxy-2α-benzoyloxy-5β,20-epoxy-1-hydroxy-10β-methoxyacetoxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate can be prepared in the following manner:

To a solution of 1.1 g of 4-acetoxy-2α-benzoyloxy-5β,20-epoxy-1-hydroxy-10β-methoxyacetoxy-7β-trifluoromethanesulphonyloxy-9-oxo-11-taxen-13α-yl (2R, 4S, 5R)-3-tert-butoxycarbonylamino-2-(4-methoxyphenyl)-4-phenyl-5-oxazolidinecarboxylate in a mixture of 11 cm$^3$ of anhydrous acetonitrile and 1.5 cm$^3$ of anhydrous tetrahydrofuran, maintained under an argon atmosphere, are added 0.2 g of powdered 4 Å molecular sieve and 0.88 g of sodium chloride. The reaction mixture is stirred for a few minutes at a temperature close to 20° C., then heated at the boiling temperature of the solvent for 2 hours. After cooling at a temperature close to 20° C., the reaction mixture is filtered and concentrated to dryness under reduced pressure. 1.5 g of a yellow oil are obtained which are purified by chromatography at atmospheric pressure on 50 g of silica gel (0.063–0.2 mm) contained in a column 3 cm in diameter, eluting with a dichloromethane-methanol mixture (9-1 by volume). 480 mg of pure 4-acetoxy-2α-benzoyloxy-5β,20-epoxy-1-hydroxy-10β-methoxyacetoxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate is obtained in the form of an ivory foam.

4-Acetoxy-2α-benzoyloxy-5β,20-epoxy-1-hydroxy-10β-methoxyacetoxy-7β-trifluoromethanesulphonyloxy-9-oxo-11-taxen-13α, 4S, 5R)-3-tert-butoxycarbonylamino-2-(4-methoxyphenyl)-4-phenyl-5-oxazolidinecarboxylate can be prepared in the following manner:

To a solution of 1.0 g of 4-acetoxy-2α-benzoyloxy-5β,20-epoxy-1,13α-dihydroxy-10β-methoxyacetoxy-7β-trifluoromethanesulphonyloxy-9-oxo-11-taxene and 0.94 g of (2R, 4S, 5R)-3-tert-butoxycarbonylamino-2-(4-methoxyphenyl)-4-phenyl-5-oxazolidinecarboxylic acid in 10 cm$^3$ of anhydrous toluene are added at a temperature close to 20° C., under an argon atmosphere, 0.3 g of powdered 4Å molecular sieve, 0.63 g of 1,3-dicyclohexylcarbodiimide and 0.15 g of 4-dimethymaminopyridine. The reaction mixture is stirred at a temperature close to 20° C. under an argon atmosphere for 30 minutes, then filtered and concentrated to dryness under reduced pressure. 2.1 g of a yellow foam are obtained which are purified by chromatography at atmospheric pressure on 60 g of silica gel (0.063–0.2 mm) contained in a column 2.5 cm in diameter, eluting with a cyclohexane-ethyl acetate mixture (1-1 by volume). 1.17 g of pure 4-acetoxy-2α-benzoyloxy-5β,20-epoxy-1-hydroxy-10β-methoxyacetoxy-7β-trifluoromethanesulphonyloxy-9-oxo-11-taxen-13α-yl (2R, 4S, 5R)-3-tert-butoxycarbonylamino-2-(methoxy-4 phenyl)-4-phenyl-5-oxazolidinecarboxylate are obtained in the form of a light yellow foam.

Example 8

180 mg of 4-acetoxy-2α-benzoyloxy-5β,20-epoxy-1-hydroxy-10β-butoxyacetoxy-7β,8β-methylene-9-oxo-19-nor-11-taxen-13α-yl (2R, 4S, 5R)-3-tert-butoxycarbonylamino-2-(4-methoxy phenyl)-4-phenyl-5-oxazolidinecarboxylate are dissolved in 3.5 cm$^3$ of 0.1N HCl in ethanol. The solution is stirred for 2 hours at a temperature close to 20° C. Then is added a mixture of 80 cm$^3$ of dichloromethane and of 10 cm$^3$ of a saturated aqueous solution of sodium hydrogen carbonate. After decantation, the aqueous phase is extracted with 10 cm$^3$ of dichloromethane. The organic phases are pooled and washed with 3 times 10 cm$^3$ of distilled water, dried over magnesium sulphate, filtered and concentrated to dryness under reduced pressure (2.7 kPa) at 40° C. 155 mg of a white foam are obtained which are purified by chromatography on 7.5 g of silica gel (0.063–0.2 mm) contained in a column 1 cm in diameter, eluting with a dichloromethane-methanol mixture (99-1 by volume) and collecting 5 cm$^3$ fractions. The fractions containing only the desired product are pooled and concentrated under reduced pressure (0.27 kPa) at 20° C. for 16 hours. 98 mg of 4-acetoxy-2α-benzoyloxy-5β,20-epoxy-1-hydroxy-10β-butoxyacetoxy-7β,8β-methylene-9-oxo-19-nor-11-taxen-13α-yl (2R,3S)-3-tert-butoxycarbonylamine-2-hydroxy-3-phenylpropionate are obtained in the form of a white foam whose characteristics are the following:

specific rotation: $[\alpha]_D^{20}$ =-32 (c=0.5, methanol)

proton NM spectrum (300 MHz, CDCl$_3$, δ in ppm, coupling constants J in Hz): 0.97 (s,3H:—OC$_4$H$_9$ (—CH$_3$); 1.28 (s,3H:—CH$_3$ 16 or 17); 1.31 (s, 12H: C(CH$_3$)$_3$ and CH$_3$ 16 or 17); 1.38 (mt, 1H: H 7); 1.43 and 1.65 (2 mt, 2H each OC$_4$H$_9$(OCH$_2$ CH$_2$CH$_2$CH$_3$); 1.72 and 2.26 (2 mt, 1H each: CH$_2$ 19); 1.87 (s, 1H: OH); 1.89 (s, 3H: —CH$_3$); 2.15 and 2.50 (respectfully broad d and dt, J=16 and J=16 and 4.5, 1H each: CH$_2$6); 2.25 and 2.41 (respectively dd and mt, J=16 and 9, 1H each: CH$_2$ 14); 2.42 (s,3H: COCH$_3$); 3.28 (mt, 1H: OH 2'); 3.65 (t,J=7.5, 2H: OC$_4$H$_9$); 4.07 and 4.35 (2 d,J=9, 1H each: CH$_2$20); 4.12 (d,J=7.5, 1H: H 3); 4.28 (AB limit, J=17, 2H OCOCH$_2$O); 4.65 (mt, 1H: H 2'); 4.76 (d,J=4.5, 1H: H 5); 5.31 (broad d,J=10, 1H: H 3'); 5.38 (d,J=10, 1H: CONH); 5.70 (d,J=7.5, 1H: H 2); 6.29 (broad t,J=9, 1H: H 13); 6.43 (s, 1H: H 10); from 7.25 to 7.45 (mt, 5H: C$_6$H$_5$3'); 7.52 [(t,J=7.5, 2H: OCOC$_6$H$_5$(H 3 and H 5)]; 7.63 [(t,J=7.5, 1H: OCOC$_6$H$_5$(H 4)]; 8.18 [(d,J=7.5, 2H: OCOC$_6$H$_5$ (H 2 and H 6)].

4-Acetoxy-2α-benzoyloxy-5β,20-epoxy-1-hydroxy-10β-butoxyacetoxy-7β,8β-methylene-9-oxo-19-nor-11-taxen- 13α-yl (2R, 4S, 5R)-3-tert-butoxycarbonylamino-2-(methoxy-4phenyl)-4-phenyl-5-oxazolidinecarboxylate can be prepared in the following manner:

To a solution of 0.015 cm³ of butoxyacetic acid in 5 cm³ of anhydrous toluene, maintained under an argon atmosphere and stirred, are added 100 mg of 4-acetoxy-2α-benzoyloxy-5β,20-epoxy-1,10β-dihydroxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate, 7 mg of 4-dimethylaminopyridine and 40 mg of 1,3-dicyclohexylcarbodiimide. The reaction mixture is stirred for 2 hours at a temperature close to 20° C. then filtered on sintered glass filter provided with celite. The filter is rinsed with 100 cm³ of ethyl acetate. The filtrates are pooled, washed with 4 times 8 cm³ of distilled water, dried over magnesium sulphate, filtered and concentrated under reduced pressure (2.7 kPa) at 40° C. 128 mg of a white foam are obtained which are purified by chromatography on 7.5 g of silica gel (0.063–0.2 mm) contained in a column 1 cm in diameter, eluting with a dichloromethane-methanol mixture (99-1 by volume) and collecting 10 cm³ fractions. The fractions containing only the desired product are pooled and concentrated under reduced pressure (2.7 kPa) at 40° C. 94 mg of 4-acetoxy-2α-benzoyloxy-5β,20-epoxy-1-hydroxy-10β-butoxyacetoxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate are obtained in the form of a white foam.

4-Acetoxy-2α-benzoyloxy-5β,20-epoxy-1,10β-dihydroxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate can be prepared in the following manner:

To a solution of 12.5 g of 4-acetoxy-2α-benzoyloxy-5β,20-epoxy-1-hydroxy-10β-methoxyacetoxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate in 850 cm³ of anhydrous methanol, maintained under an argon atmosphere, are added at a temperature close to 20° C., 37.5 g of powdered 4Å molecular sieve and 6.52 g of zinc iodide. The reaction mixture is stirred for 5 hours at a temperature close to 20° C. and then concentrated to dryness under reduced pressure (2.7 kPa) at 40° C. The solid obtained is dissolved in 850 cm³ of ethyl acetate and 150 cm³ of distilled water are added. The reaction mixture is stirred for 10 minutes and the insoluble material is filtered on sintered glass filter. The sintered glass filter is rinsed with 100 cm³ of ethyl acetate. The filtrates are pooled and the aqueous phase is separated by decantation and extracted with 100 cm³ of ethyl acetate. The organic phases are pooled, washed with 3 times of distilled water, dried over magnesium sulphate, filtered and concentrated under reduced pressure (2.7 kPa) at 40° C. 12.2 g of a yellow foam are obtained which are purified by chromatography on 425 g of silica gel (0.063–0.2 mm) contained in a column 6 cm in diameter, eluting with a dichloromethane-methanol mixture (99-1 by volume) and collecting 100 cm³ fractions. The fractions containing only the desired product are pooled and concentrated under reduced pressure (0.27 kPa) at 20° C. for 16 hours. 8.62 g of 4-acetoxy-2α-benzoyloxy-5β,20-epoxy-1,10β-dihydroxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate are obtained in the form of a white foam.

4-Acetoxy-2α-benzoyloxy-5β,20-epoxy-1-hydroxy-10β-methoxyacetoxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate can be prepared in the following manner:

To a solution of 8.24 g of (2R, 4S, 5R)-3-tert butoxycarbonylamino-2-(4-methoxyphenyl)-4-phenyl-5-oxazolidinecarboxylic acid in 470 cm³ of ethyl acetate, maintained under an argon atmosphere and stirred, are added, at a temperature close to 20° C., 10.33 g of 4-acetoxy-2α-benzoyloxy-5β,20-epoxy-1,13α-dihydroxy-10β-methoxyacetoxy-7β,8β-methylene-9-oxo-19-nor-11-taxene, 1.1 g of 4-dimethylaminopyridine and 6.23 g of 1,3-dicyclohexylcarbodiimide. The reaction mixture is stirred for 2 hours at a temperature close to 20° C., then filtered on sintered filter glass provided with celite. The sintered glass filter is washed with 3 times 100 cm³ of ethyl acetate. The filtrates are pooled, washed successively with 3 times 150 cm³ of distilled water, 100 cm³ of a saturated solution of sodium hydrogen carbonate and with twice 150 cm³ of distilled water, dried over magnesium sulphate, filtered and concentrated to dryness under reduced pressure (2.7 kPa) at 40° C. 21.2 g of a yellow foam are obtained which are purified by chromatography on 900 g of silica gel (0.063–0.2 mm) contained in a column 7 cm in diameter, eluting with a dichloromethane-methanol mixture (99-1 by volume) and collecting 100 cm³ fractions. The fractions containing only the desired product are pooled and concentrated under reduced pressure (0.27 kPa) at 40° C. 15.47 g of 4-acetoxy-2α-benzoyloxy-5β,20-epoxy-1-hydroxy-10β-methoxyacetoxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate are obtained in the form of a white foam.

(2R, 4S, 5R)-3-tert-butoxycarbonylamino-2-(4-methoxyphenyl)-4-phenyl-5-oxazolidine-carboxylic acid can be prepared in the following manner:

A solution of 10.0 g of methyl (2R,3S)-3-tert-butoxycarbonylamino-2-hydroxy-3-phenylpropionate and of 0.25 g of pyridinium 4-toluenesulphonate in 200 cm³ of toluene is dehydrated by distillation of 20 cm³ of solvent. 6.34 cm³ of 4-methoxybenzaldehyde dimethylacetate is added in the course of 5 minutes and the reaction mixture heated at the boiling temperature. During the addition, 50 cm³ of solvent are distilled and then 100 cm³ of solvent are still distilled. After cooling at a temperature close to 20° C., 80 cm³ of cyclohexane are added in the course of 10 minutes. The reaction mixture is cooled to 0–5° C. and filtered on sintered glass filter. The precipitate is washed with 40 cm³ of cyclohexane and dried under reduced pressure at a temperature close to 20° C. 10.9 g of (2R, 4S, 5 R)-3-tert-butoxycarbonylamino-2-(4-methoxyphenyl)-4-phenyl-5-oxazolidine-carboxylic acid are obtained in 74% yield.

4-Acetoxy-2α-benzoyloxy-5β,20-epoxy-1,13α-dihydroxy-10β-methoxyacetoxy-7β,8β-methylene-9-oxo-19-nor-11-taxene can be prepared in the following manner:

To a solution of 15.37 g of 4-acetoxy-2α-benzoyloxy-5β,20-epoxy-1,13α-dihydroxy-10β-methoxyacetoxy-7β-trifluoromethanesulphonyloxy-9-oxo-11-taxene in a mixture of 310 cm³ of acetonitrile and of 31 cm³ of anhydrous tetrahydrofuran, maintained under an argon atmosphere and stirred, are added 9 g of powdered 4Å molecular sieve and 24 g of sodium chloride. The reaction mixture is stirred for 30 minutes at a temperature close to 20° C. and then at the boiling point (75° C.) for 2.5 hours. After cooling at a temperature close to 20° C., the reaction mixture is filtered on sintered glass filter.- The sintered glass filter is washed with 4 times 400 cm³ and the pooled filtrates are washed successively with 4 times 300 cm³ of distilled water, 250 cm³ of a saturated solution of sodium hydrogen carbonate and with 250 cm³ of distilled water, dried over magnesium sulphate, filtered and concentrated to dryness under reduced pressure (2.7 kPa) at 40° C. 2.12 g of a white foam are obtained which are purified by chromatography on 750 g of silica gel (0.063–0.2 mm) contained in a column 6 cm in diameter, eluting with a dichloromethane-methanol mixture (99-1 by volume) and collecting 100 cm³ fractions. The fractions containing only the desired product are pooled and concentrated under reduced pressure (0.27 kPa) at 40° C. 10.35 g of 4-acetoxy-2α-benzoyloxy-5β,20-epoxy-1,13α-dihydroxy-10β-methoxyacetoxy-7β,8β-methylene-9-oxo-19-nor-11-taxene are obtained in the form of a white foam.

4-Acetoxy-2α-benzoyloxy-5β,20-epoxy-1,13α-dihydroxy-10β-methoxyacetoxy-7β-trifluoromethanesulphonyloxy-9-oxo-11-taxene can be prepared in the following manner:

To a solution of 19.1 g of 4-acetoxy-2α-benzoyloxy-5β,20-epoxy-1,7β,13α-trihydroxy-10β-methoxyacetoxy-9-oxo-11-taxene in 900 cm³ of dichloromethane, maintained under an argon atmosphere and stirred, are added, at a temperature close to 20° C., 9.9 cm³ of anhydrous pyridine and then, slowly, 6.3 cm³ of trifluoromethanesulphonic anhydride. The reaction mixture is stirred for 15 minutes at a temperature close to 20° C. and then heated to 40° C. for 2 hours. After cooling at a temperature close to 20° C., the reaction mixture is poured in 250 cm³ of distilled water. The aqueous phase is separated by decantation and extracted with twice 30 cm³ of dichloromethane. The organic phases are pooled, dried over magnesium sulphate, filtered and concentrated under reduced pressure (2.7 kPa) at 40° C. 25.12 g of an orange foam are obtained which are purified by chromatography on 900 g of silica gel (0.063–0.2 mm) contained in a column 6.5 cm in diameter, eluting with a dichloromethane-methanol mixture (99-1 by volume) and collecting 100 cm³ fractions. The fractions containing only the desired product are pooled and concentrated under reduced pressure (2.7 kPa) at 40° C. 15.37 g of 4-acetoxy-2α-benzoyloxy-5β,20-epoxy-1,13α-dihydroxy-10β-methoxyacetoxy-7β-trifluoromethanesulphonyloxy-9-oxo-11-taxene are obtained.

4-Acetoxy-2α-benzoyloxy-5β,20-epoxy-1,7β,13α-trihydroxy-10β-methoxyacetoxy-9-oxo-11-taxene can be prepared in the following manner:

To a solution of 22.4 g of 4-acetoxy-2α-benzoyloxy-5β-20-epoxy-1,13α-dihydroxy-7β-triethylsilyloxy-10β-methoxyacetoxy-9-oxo-11-taxene in 225 cm3 of dichloromethane, maintained under an argon atmosphere and stirred, are added dropwise at a temperature close to 0° C., 374 cm3 of a complex of fluorhydric acid and triethylamine (3-1 by mole). The reaction mixture is heated to a temperature close to 20° C. and maintained at this temperature for 2.5 hours and then, maintaining the temperature close to 20° C., poured in 1800 cm³ of a saturated solution of sodium hydrogen carbonate. The pH of the aqueous phase is adjusted to 7–8 by addition, very slowly and under vigorous stirring, of 200 g of sodium hydrogen carbonate. The 350 cm³ of dichloromethane are added and the insoluble material is separated by filtration on a sintered glass filter. The sintered glass filter is washed twice with 100 cm³ of dichloromethane. The aqueous phase is separated by decantation and extracted with twice 200 cm³ of dichloromethane. The organic phases are pooled and washed with 3 times 150 cm³ of distilled water, dried over magnesium sulphate, filtered and concentrated under reduced pressure (2.7 kPa) at 40° C. 19.1 g of 4-acetoxy-2α-benzoyoloxy-5β,20-epoxy-1,7β,13α-trihydroxy-10β-methoxyacetoxy-9-oxo-11-taxene are obtained in the form of a beige foam.

4-Acetoxy-2α-benzoyloxy-5β,20-epoxy-1,13α-dihydroxy-7β-triethylsilyloxy-10β-methoxyacetoxy-9-oxo-11-taxene can be prepared in the following manner:

To a solution of 43.5 g of 4-acetoxy-2α-benzoyloxy-5β,20-epoxy-1,10β,13α-trihydroxy-7β-triethylsilyloxy-9-oxo-11-taxene in 500 cm³ of anhydrous pyridine, maintained under under an argon atmosphere and stirred, are added dropwise, in the course of 75 minutes and at a temperature close to 5° C., 430 g of methoxyacetic chloride. The reaction mixture is heated at 20° C., stirred for 24 hours and then poured in 8000 cm³ of water at a temperature close to 5° C. After 15 minutes the reaction mixture is filtered on sintered glass filter. The sintered glass filter is washed with 3 times 250 cm³ of ethyl acetate. The decanted organic phase is washed with 4 times 500 cm³ of distilled water, dried over magnesium sulphate and concentrated to dryness under reduced pressure (2.7 kPa) at 40° C. 92 g of a brown foam is obtained which is taken in 250 cm³ of diisopropyl ether. The suspension is stirred for 1 hour at a temperature close to 20° C., filtered on a sintered glass filter, washed with twice 100 cm³ of diisopropyl ether and dried under reduced pressure (2.7 kPa) at 20° C. for 16 hours. 69 g of 4-acetoxy-2α-benzoyloxy-5β,20-epoxy-1,13α-dihydroxy-7β-triethylsilyloxy-10β-methoxyacetoxy-9-oxo-11-taxene are obtained in the form of a beige foam.

4-Acetoxy-2α-benzoyloxy-5β,20-epoxy-1-10β,13α-trihydroxy-7β-triethylsilyloxy-9-oxo-11-taxene can be prepared according to the method described by J -N. Denis et al., J. Amer. Chem. Soc., 110 5917–5919 (1988).

Example 9

Using the procedure described in Example 8 but starting with 168 mg of 4-acetoxy-2α-benzoyloxy-5β,20-epoxy-1-hydroxy-10β-ethoxyacetoxy-7β,8β-methylene-9-oxo-19-nor-11-taxen-13α-yl (2R, 4S, 5 R)-3-tert-butoxycarbonylamino-2-(4-methoxyphenyl)-4-phenyl-5-oxazolidinecarboxylate, 97 mg of 4-acetoxy-2α-benzoyloxy-5β,20-epoxy-1-hydroxy-10β-ethoxyacetoxy-7β,8β-methylene-9-oxo-19-nor-11-taxen-13α-yl (2R,3S)-3-tert-butoxycarbonylamino-2-hydroxy-3-phenylpropionate are obtained in the form of a white foam whose characteristics are the following:

specific rotation: $[\alpha]_D^{20}$=−34 (c=0.5, methanol)

proton NMR spectrum (300 MHz, CDCl$_3$, δ in ppm, coupling (constants J in Hz) 1.28 (s, 3H: CH$_3$ 16 or 17); 1.31 (s, 15H: C(CH$_3$)$_3$, OCH$_2$CH$_3$ and CH$_3$ 16 or 17); 1.42 (mt, 1H: H 7); 1.72 and 2.26 (respectively dd and mt, J=7 and 5, 1H each: CH$_2$ 19); 1.87 (s, 1H: OH 1); 1.89 (s, 3H: CH$_3$); 2.15 and 2.50 (respectively: broad d and dt, J=16 and J=16 and 4.5, 1H each: CH$_2$ 6); 2.26 and 2.41 (respectively dd and mt, J=16 and 9, 1H each: CH$_2$ 14); 2.41 (s, 3H: COCH$_3$); 3.28 (mt, 1H: OH 2'); 3.71 (q,J=7.5, 2H: OCH$_2$CH$_3$); 4.05 and 4.35 (2 d,J=9, 1H each: CH$_2$ 20); 4.14 (d,J=7.5, 1H: H3); 4.30 (AB limit, J=17, 2H: OCOCH$_2$O); 4.63 (mt, 1H: H 2'); 4.76 (d,J=4.5 Hz, 1H: H 5); 5.29 (broad d,J=10, 1H: H 3'); 5.38 (d,J=10, 1H: CONH); 5.70 (d,J=7.5, 1H: H 2); 6.30 (broad t; J=9, 1H: H 13); 6.45 (s, 1H H 10); from 7.30 to 7.50 (mt, 5H: C$_6$H$_5$3'); 7.54 [(t,J=7.5, 2H: OCOC$_6$H5 (H3 and H5)]; 7.62 (t,J=7.5, 1H: OCOC$_6$H$_5$(H4)]; 8.18 [(d,J=7.5 2H: OCOC$_6$H$_5$(H 2 and H 6)].

Using the procedure described in Example C but starting with 200 mg of 4-acetoxy-2α-benzoyloxy-5β,20-epoxy-1,10β-dihydroxy-7β,8β-methylene-9-oxo-19-nor-11-taxen-13α-yl(2R, 4S, 5 R)-3-tert-butoxycarbonylamino-2-(4-methoxyphenyl)-4-phenyl-5-oxazolidinecarboxylate, 168 mg of 4-acetoxy-2α-benzoyloxy-5β,20-epoxy-1-hydroxy-10β-ethoxyacetoxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate in the form of a white foam.

Example 10

Using the procedure described in Example 8 but starting with 253 mg of 4-acetoxy-2α-benzoyloxy-5β,20-epoxy-1-hydroxy-10β-isopropoxyacetoxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate, 156 mg of 4-acetoxy-2α-benzoyloxy-5β,20-epoxy-1-hydroxy-10β-isopropoxyacetoxy-7β,8β-methylene-9-oxo-19-nor-11-taxen-13α-yl (2R,3S)-3-tert-butoxycarbonylamino-2-hydroxy-3-phenylpropionate are obtained in the form of a white foam whose characteristics are the following:

specific rotation: $[\alpha]_D^{20} = -39$ (c=0.5, methanol)

proton NMR spectrum (300 MHz, CDCl$_3$, δ in ppm, coupling constants J in Hz) From 1.20 to 1.45 (mt, 21H: CH$_3$ 16 or 17, CH$_3$ 16 or 17, —C(CH$_3$)$_3$ and —OCH(CH$_3$)$_2$); 1.38 (mt, 1H: H 7); 1.68 and 2.26 (respectively dd and mt, J=6.5 and 5.5, 1H each: CH$_2$ 19); 1.84 (s, 1H: OH 1); 1.87 (s, 3H: CH$_3$); 2.10 and 2.47 (respectively broad d and dt, J=16 and J=16 and 4.5, 1H each: CH$_2$ 6); 2.24 and 2.39 (respectively dd and mt, J=16 and 9, 1H each: CH$_2$ 14); 2.40 (s, 3H: COCH$_3$); 3.25 (mt, 1H: OH 2'); 3.78 [(mt, 1H: OCH(CH$_3$)$_3$]; 4.03 and 4.32 (2 d,J=9, 1H each: CH$_2$ 20); 4.10 (d,J=7.5, 1H: H 3); 4.26 (AB limit, J=16, 2H: OCOCH$_2$O); 4.62 (mt, 1H: H 2'); 4.73 (d,J=4.5, 1H: H 5); 5.29 (broad d,J=10, 1H: H 3'); 5.35 (d,J=10, 1H: CONH); 5.67 (d, J=7.5, 1H: H 2); 6.27 (broad t,J=9, 1H H 13) 6.41 (s, 1H: H 10); from 7.25 to 7.50 (mt, 5H C$_6$H$_5$ 3'); 7.51 [t,J=7.5, 2H: OCOC$_6$H$_5$(H3 and H 5)]; 7.61 [t,J=7.5, 1H: OCOC$_6$H$_5$(H 4)]; 8.16 [(d,J=7.5, 2H: OCOC$_6$H$_5$(H 2 and H 6)].

Using the procedure described in Example C but starting with 300 mg of 4-acetoxy-2α-benzoyloxy-5β,20-epoxy-1,10β-dihydroxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate, 253 mg of 4-acetoxy-2α-benzoyloxy-5β,20-epoxy-1-hydroxy-10β-isopropoxyacetoxy-7β,8β-methylene-9-oxo-19-nor-11-taxen-13α-yl (2R, 4S, 5R)-3-tert-butoxycarbonylamino-2-(4-methoxyphenyl)-4-phenyl-5-oxazolidinecarboxylate in the form of a white foam.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A process for preparing a compound of formula III:

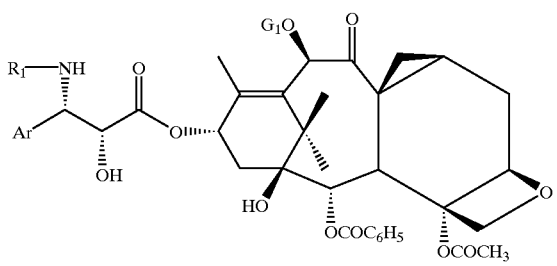

III in which Ar represents an aryl radical,

R$_1$ represents a benzoyl radical or a radical R$_2$—O—CO in which R$_2$ represents an alkyl, alkenyl, alkynyl, cycloalkenyl, bicycloalkyl, phenyl, or heterocyclic radical; and G$_1$ represents a hydrogen atom or an acetyl, alkoxyacetyl or alkyl radical, or other hydroxy-protecting group;

comprising a) treating in an acidic medium a compound of formula II,

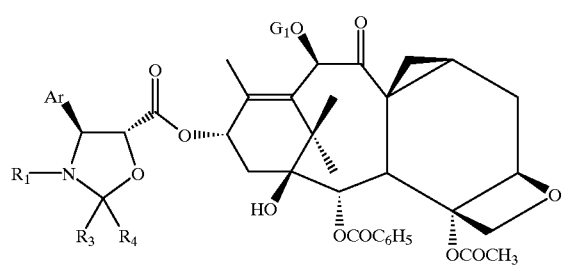

II in which Ar represents an aryl radical;

R$_1$ represents a benzoyl radical or a radical R$_2$—O—CO in which R$_2$ represents an alkyl, alkenyl, alkynyl, cycloalkyl, cyclokenyl, bicycloalkyl, phenyl or heterocyclyl radical;

R$_3$ and R$_4$, which are identical or different, each independently represent a hydrogen atom, or an alkyl radical containing 1 to 4 carbon atoms, or an aralkyl radical in which the alkyl portion contains 1 to 4 carbon atoms and the aryl portion is unsubstituted or substituted by one or more alkoxy radicals containing 1 to 4 carbon atoms, or an aryl radical unsubstituted or substituted by one or more alkoxy radicals containing 1 to 4 carbon atoms; or R$_3$ represents an alkoxy radical containing 1 to 4 carbon atoms or a trihalomethyl radical or a phenyl radical substituted by a trihalomethyl radical and R$_4$ represents a hydrogen atom; or R$_3$ and R$_4$ form, together with the carbon atom to which they are bound, a cyclic radical with 4 to 7 members; and G$_1$ represents a hydrogen atom or an acetyl, alkoxyacetyl or alkyl radical, or other hydroxy-protecting group; to yield the compound of formula III.

2. The process of claim 1, in which R$_3$ of the compound of formula II represents a hydrogen atom or an alkoxy radical containing 1 to 4 carbon atoms or an aryl radical unsubstituted or substituted by one or more alkoxy radicals containing 1 to 4 carbon atoms, and R$_4$ of the compound of formula II represents a hydrogen atom.

3. The process of claim 1, wherein when G$_1$ in the compound of formula III represents a hydrogen atom, further reacting said compound of formula III, with an alkoxyacetylating agent to yield a compound of formula III in which G$_1$ represents an alkoxyacetyl radical.

4. The process of claim 3, in which the alkoxyacetyl radical contains 1 to 8 carbon atoms, and is branched or unbranched.

5. The process of claim 4, in which the alkoxyacetyl radical is methoxyacetyl, ethoxyacetyl, isopropoxyacetyl, or butoxyacetyl.

6. The process of claim 1, wherein when G$_1$ in the compound of formula III represents an acetyl, alkoxyacetyl, or alkyl radical, or other hydroxy-protecting group, further comprising replacing G$_1$ with a hydrogen atom.

7. The process of claim 6, in which $G_1$ represents 2,2,2-trichloroethoxycarbonyl, or 2-(2-trichloromethylpropoxy)carbonyl radical.

8. A process for preparing a compound of formula III,

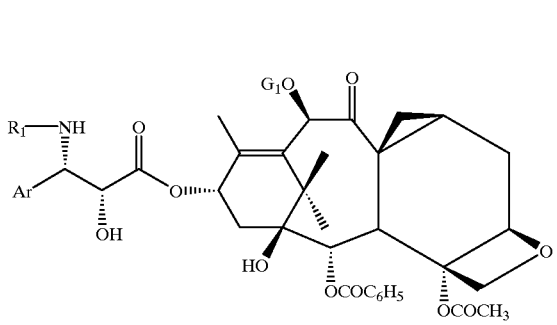

in which Ar represents an aryl radical;

$R_1$ represents a benzoyl radical or a radical $R_2$—O—CO in which $R_2$ represents an alkyl, alkenyl, alkynyl, cycloalkyl, cycloalkenyl, bicycloalkyl, phenyl or heterocyclyl radical; and $G_1$ represents a hydrogen atom or an acetyl, alkoxyacetyl or alkyl radical, or other hydroxy-protecting group;

comprising:

a) treating in an acidic medium a compound of formula II:

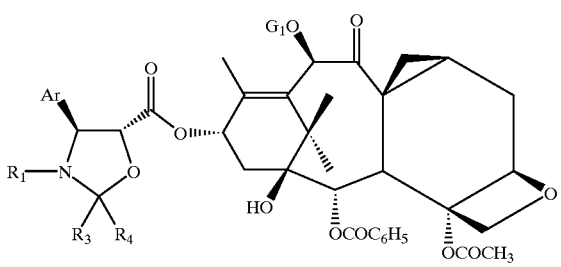

in which Ar represents an aryl radical;

$R_1$ represents a benzoyl radical or a $R_2$—O—CO radical in which $R_2$ represents an alkyl, alkenyl, alkynyl, cycloalkyl, cycloalkenyl, bicycloalkyl, phenyl or heterocyclyl radical;

$G_1$ represents a hydrogen atom or an acetyl, alkoxyacetyl or alkyl radical, or other hydroxy-protecting group;

and $R_3$ and $R_4$, which are identical or different, each independently represent
an alkyl radical;
an aralkyl radical, or
an aryl radical; or $R_3$ represents a trihalomethyl radical or a phenyl radical substituted by a trihalomethyl radical and $R_4$ represents a hydrogen atom;

$R_3$ and $R_4$ form, together with the carbon atom to which they are bound, a cyclic radical with 4 to 7 members, to yield a compound of formula IV:

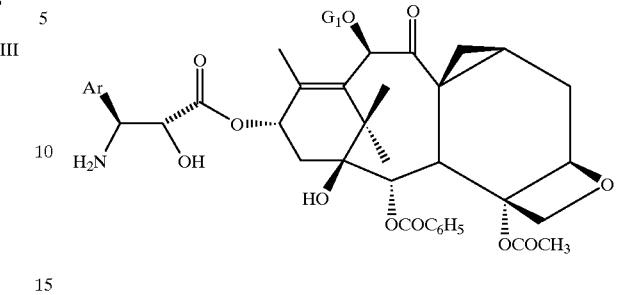

in which Ar and $G_1$ are defined as in formula II;

b) acylating the compound of formula II with benzoyl chloride or with a reactant of formula V:

$$R_2—O—CO—X \qquad V$$

in which $R_2$ represents an alkyl, alkenyl alkynyl, cyclokenyl, bicycloalkyl, phenyl, or heterocyclic radical, and X represents a halogen atom or a radical —O—$R_2$ or —O—CO—O—$R_2$, to yield the compound of formula III.

9. The process of claim 8, wherein when $R_3$ or $R_4$ within the compound of formula II represents an alkyl radical, said alkyl radical contains 1 to 4 carbon atoms.

10. The process of claim 8, wherein when $R_3$ or $R_4$ within the compound of formula II represents an aralkyl radical, said aralkyl radical contains:
an alkyl portion which contains 1 to 4 carbon atoms, and
an aryl portion which is a phenyl radical unsubstituted or substituted by one or more alkoxy radicals which contains 1 to 4 carbon atoms.

11. The process of claim 8, wherein when $G_1$ of the compound of formula III represents an acetyl, alkoxyacetyl, or alkyl radical, or other hydroxy protecting group, replacing $G_1$ with a hydrogen atom.

12. A method of treating a human or animal patient with at least one tumor exhibiting multi-drug resistance, comprising administering to the patient an efficacious amount of a compound of formula (I):

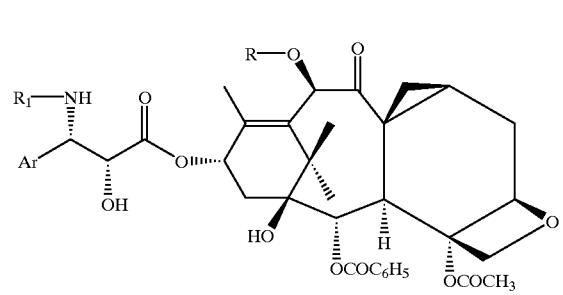

in which
R represented an alkoxyacetyl radical,
$R_1$ represents a benzoyl radical or a radical $R_2$—O—CO in which $R_2$ represents an alkyl, alkenyl, cycloalkyl, cycloalkenyl, bicycloalkyl, phenyl or heterocyclyl radical, and
Ar represents an aryl radical.

* * * * *